(12) United States Patent
Brown et al.

(10) Patent No.: US 8,742,124 B2
(45) Date of Patent: *Jun. 3, 2014

(54) AMIDE DERIVATIVES BEARING A CYCLOPROPYLAMINOACARBONYL SUBSTITUENT USEFUL AS CYTOKINE INHIBITORS

(71) Applicant: AstraZeneca AB, Södertälje (SE)

(72) Inventors: Dearg Sutherland Brown, Macclesfield (GB); John Graham Cumming, Macclesfield (GB); Ian Alun Nash, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/628,958

(22) Filed: Sep. 27, 2012

(65) Prior Publication Data

US 2013/0035346 A1 Feb. 7, 2013

Related U.S. Application Data

(63) Continuation of application No. 13/080,583, filed on Apr. 5, 2011, now abandoned, which is a continuation of application No. 10/581,305, filed as application No. PCT/GB2004/005241 on Dec. 15, 2004, now Pat. No. 7,943,776.

(30) Foreign Application Priority Data

Dec. 20, 2003 (GB) .................................. 0329572.2

(51) Int. Cl.
 *C07D 213/56* (2006.01)

(52) U.S. Cl.
 USPC ............................ 546/337; 546/336; 546/329

(58) Field of Classification Search
 USPC .......................................... 546/337, 336, 329
 See application file for complete search history.

(56) References Cited

U.S. PATENT DOCUMENTS

| 6,821,965 | B1 | 11/2004 | Brown et al. |
| 2005/0038081 | A1 | 2/2005 | Brown et al. |

FOREIGN PATENT DOCUMENTS

| WO | WO 00/07980 A2 | 2/2000 |
| WO | WO 01/70671 A2 | 9/2001 |
| WO | WO 2004/071440 A2 | 8/2004 |
| WO | WO 2004/098158 A2 | 11/2004 |
| WO | WO 2005/042502 A1 | 5/2005 |

OTHER PUBLICATIONS

Boehm, J. C. et al., "New Inhibitors of p38 Kinase" Expert Opinion of Therapeutic Patents, Ashley Publications, GB, vol. 10, No. 1, 2000, pp. 25-37, XP002259248 ISSN: 1354-3776.

*Primary Examiner* — Andrew D Kosar
*Assistant Examiner* — Raymond Covington
(74) *Attorney, Agent, or Firm* — Dechert LLP

(57) ABSTRACT

The invention concerns a compound of the Formula (I), wherein Qa is heteroaryl and is substituted with halogeno; R1 and R2 are hydrogen; and Qb is phenyl or heteroaryl, and Qb may optionally bear 1 or 2 substituents selected from hydroxy, halogeno and (1-6C)alkyl, or a pharmaceutically-acceptable salt thereof; processes for their preparation, pharmaceutical compositions containing them and their use in the treatment of diseases or medical conditions mediated by cytokines.

9 Claims, No Drawings

AMIDE DERIVATIVES BEARING A CYCLOPROPYLAMINOACARBONYL SUBSTITUENT USEFUL AS CYTOKINE INHIBITORS

CROSS REFERENCE TO RELATED APPLICATIONS

This application is a continuation of U.S. application Ser. No. 13/080,583, filed Apr. 5, 2011, which is a continuation of U.S. application Ser. No. 10/581,305, filed Oct. 12, 2006, which is a U.S. national phase under 35 U.S.C. §371 of International application serial no. PCT/GB2004/005241, filed Dec. 15, 2004, which claims the benefit of United Kingdom application serial no. 0329572.2, filed Dec. 20, 2003, the disclosures of each are incorporated herein by reference in their entirety.

This invention relates to amide derivatives, or pharmaceutically-acceptable salts thereof, which are useful as inhibitors of cytokine mediated disease. The invention also relates to processes for the manufacture of said amide derivatives, to pharmaceutical compositions containing said amide derivatives and to their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the amide derivatives of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis, chronic obstructive pulmonary disease and adult respiratory distress syndrome), and in the production and development of various cardiovascular and cerebrovascular disorders such as congestive heart failure, acute heart failure, myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), chronic obstructive pulmonary disease, tumour invasiveness and tumour metastasis and multiple sclerosis. Excessive cytokine production has also been implicated in pain.

Evidence of the central role played by TNFα in the cell signalling cascade which gives rise to rheumatoid arthritis is provided by the efficacy in clinical studies of antibodies of TNFα (*The Lancet*, 1994, 344, 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the amide derivatives disclosed in the present invention possesses pharmacological activity only by virtue of an effect on a single biological process, it is believed that the amide derivatives inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed in *Exp. Onin. Ther. Patents*, 2000, 10(1), 25-37. p38 kinase is known to exist in isoforms identified as p38α and p38β.

The amide derivatives disclosed in the present invention are inhibitors of the production of cytokines such as TNF, in particular of TNFα, and various interleukins, in particular IL-1.

It is known from the International Patent Application WO 00/07980 that certain amide derivatives are inhibitors of the production of cytokines such as TNF, and various interleukins. One of the disclosed compounds is N-cyclobutyl-3-(3, 4-dimethoxybenzamido)-4-methylbenzamide (Comparator Compound X).

There is no disclosure in this document of an amide derivative which bears a cyclopropylaminocarbonyl substituent at the 3-position of the central 6-methylphenyl core. We have now found that such compounds possess potent cytokine inhibitory activity and have desirable activity profiles.

Subsequently, International Patent Application WO 2004/071440 has disclosed amide derivatives that bear a cycloalkylaminocarbonyl substituent at the 3-position of the central 6-methylphenyl core. However, this application discloses thiazolyl-based compounds, wherein the thiazole ring is mainly substituted with a substituted amino group.

According to the present invention there is provided a compound of the Formula I

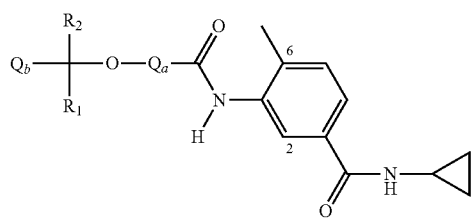

wherein
$Q_a$ is phenyl or heteroaryl, and $Q_a$ may optionally bear 1 or 2 substituents selected from hydroxy, halogeno, trifluoromethyl, cyano, amino, (1-6C)alkyl, (2-6C)alkenyl, (2-6C)alkynyl, (1-6C)alkoxy, (1-6C)alkylamino, di-[(1-6C)alkyl]amino and (1-6C)alkoxycarbonyl;
$R_1$ and $R_2$ are each independently selected from hydrogen, (1-6C)alkyl, (2-6C)alkenyl and (2-6C)alkynyl; and
$Q_b$ is phenyl, heteroaryl or heterocyclyl, and $Q_b$ may optionally bear 1 or 2 substituents selected from hydroxy, halogen, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;
and wherein any of the substituents on $Q_a$ or $Q_b$ defined hereinbefore which comprise a $CH_2$ group which is attached to 2 carbon atoms or a $CH_3$ group which is attached to a carbon atom may optionally bear on each said $CH_2$ or $CH_3$ group one or more substituents selected from hydroxy, cyano, amino, (1-6C)alkyl, (1-6C)alkoxy, (1-6C)alkylamino and di-[(1-6C)alkyl]amino;
or a pharmaceutically-acceptable salt thereof.

According to a further aspect of present invention there is provided a compound of the Formula I wherein
$Q_a$ is phenyl, pyridyl, pyrimidinyl, pyrazinyl or pyridazinyl, and $Q_a$ may optionally bear 1 or 2 substituents selected from halogeno, (1-6C)alkyl and (1-6C)alkoxy;
$R_1$ and $R_2$ are each independently selected from hydrogen, (1-6C)alkyl, (2-6C)alkenyl and (2-6C)alkynyl; and
$Q_b$ is phenyl, heteroaryl or heterocyclyl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;
and wherein any of the substituents on $Q_a$ or $Q_b$ defined hereinbefore which comprise a $CH_2$ group which is attached to 2 carbon atoms or a $CH_3$ group which is attached to a carbon atom may optionally bear on each said $CH_2$ or $CH_3$ group one or more substituents selected from hydroxy, cyano, amino, (1-6C)alkyl, (1-6C)alkoxy, (1-6C)alkylamino and di-[(1-6C)alkyl]amino;
or a pharmaceutically-acceptable salt thereof.

In this specification, the term (1-6C)alkyl includes straight-chain and branched-chain alkyl groups such as propyl, isopropyl and tert-butyl. References to individual alkyl groups such as "propyl" are specific for the straight-chain version only, references to individual branched-chain alkyl groups such as "isopropyl" are specific for the branched-chain version only. In this specification, the term (3-6C)cycloalkoxy includes cyclopropyloxy, cyclobutyloxy, cyclopentyloxy and cyclohexyloxy. References to individual cycloalkyl groups such as "cyclopentyl" are specific for that 5-membered ring only.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

A suitable value for $Q_a$ or $Q_b$ when it is heteroaryl is, for example, an aromatic 5- or 6-membered monocyclic ring, a 9- or 10-membered bicyclic ring or a 13- or 14-membered tricyclic ring each with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, carbazolyl, dibenzofuranyl, dibenzothiophenyl, S,S-dioxodibenzothiophenyl, xanthenyl, dibenzo-1,4-dioxinyl, phenoxathiinyl, phenoxazinyl, dibenzothiinyl, phenothiazinyl, thianthrenyl, benzofuropyridyl, pyridoindolyl, acridinyl or phenanthridinyl, preferably furyl, thienyl, oxazolyl, isoxazolyl, imidazolyl, pyrido[1,2-a]imidazolyl, pyrazolyl, thiadiazolyl, isothiazolyl, pyridyl, pyridazinyl, pyrimidinyl or pyrazinyl, more preferably furyl, isoxazolyl, thiazolyl, pyrido[1,2-a]imidazolyl, thiadiazolyl or pyridyl, pyridazinyl, pyrimidinyl or pyrazinyl.

A suitable value for $Q_b$ when it is heterocyclyl is, for example, a non-aromatic saturated or partially saturated 3- to 10-membered monocyclic or bicyclic ring or a 5- to 7-membered monocyclic ring each with up to five heteroatoms selected from oxygen, nitrogen and sulphur, for example oxiranyl, oxetanyl, azetidinyl, tetrahydrofuranyl, tetrahydropyranyl, pyrrolinyl, pyrrolidinyl, imidazolinyl, imidazolidinyl, pyrazolinyl, pyrazolidinyl, 1,1-dioxidoisothiazolidinyl, morpholinyl, thiomorpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl or benzo derivatives thereof such as 2,3-dihydrobenzofuranyl, 2,3-dihydrobenzothienyl, indolinyl, isoindolinyl, chromanyl and isochromanyl, preferably azetidin-1-yl, 3-pyrrolin-1-yl, pyrrolidin-1-yl, pyrrolidin-2-yl, 1,1-dioxidoisothiazolidin-2-yl, morpholino, 1,1-dioxotetrahydro-4H-1,4-thiazin-4-yl, piperidin-3-yl, piperidin-4-yl, homopiperidin-1-yl, piperidino, piperazin-1-yl or homopiperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

Suitable values for various substituents on $Q_a$ or $Q_b$ or for $R_1$ and $R_2$ include:—

A suitable value for a substituent on $Q_b$ when it is (3-6C)cycloalkyl-(1-6C)alkyl is, for example, cyclopropylmethyl, cyclobutylmethyl, cyclopentylmethyl, cyclohexylmethyl, cyclopropylethyl, preferably cyclopropylmethyl or cyclopropylethyl, more preferably cyclopropylmethyl.

A suitable pharmaceutically-acceptable salt of a compound of the Formula I, for example, an acid-addition salt of a compound of the Formula I which is sufficiently basic, for example, an acid-addition salt with an inorganic or organic acid such as hydrochloric, hydrobromic, sulphuric, phosphoric, trifluoroacetic, citric, maleic, tartaric, fumaric, hemifumaric, succinic, hemisuccinic, mandelic, methanesulphonic, dimethanesulphonic, ethane-1,2-sulphonic, benzenesulphonic, salicylic or 4-toluenesulphonic acid.

Further values of $Q_a$, $Q_b$, $R_1$ and $R_2$ are as follows. Such values may be used where appropriate with any of the definitions, claims or embodiments defined hereinbefore or hereinafter.

$Q_a$ is phenyl or heteroaryl, and $Q_a$ may optionally bear 1 or 2 substituents selected from hydroxy, halogen, trifluorom-

| | |
|---|---|
| for halogeno: | fluoro, chloro, bromo and iodo; |
| for (1-6C)alkyl: | methyl, ethyl, propyl, isopropyl and tert-butyl; |
| for (2-6C)alkenyl: | vinyl and allyl; |
| for (2-6C)alkynyl: | ethynyl and 2-propynyl; |
| for (1-6C)alkoxy: | methoxy, ethoxy, propoxy, isopropoxy and butoxy; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl and propionyl; |
| for (1-6C)alkylamino: | methylamino, ethylamino and propylamino; |
| for di-[(1-6C)alkyl]amino: | dimethylamino, diethylamino and N-ethyl-N-methylamino; |
| for halogeno-(1-6C)alkyl: | fluoromethyl, chloromethyl, bromomethyl, difluoromethyl, dichloromethyl, dibromomethyl, 2-fluoroethyl, 2-chloroethyl and 2-bromoethyl; |
| for hydroxy-(1-6C)alkyl: | hydroxymethyl, 2-hydroxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for cyano-(1-6C)alkyl: | cyanomethyl, 2-cyanoethyl, 1-cyanoethyl and 3-cyanopropyl; |
| for amino-(1-6C)alkyl: | aminomethyl, 2-aminoethyl, 1-aminoethyl and 3-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl. |
| for (2-6C)alkanoyloxy: | acetoxy and propionyloxy: |
| for (1-6C)alkanoylamino: | formamido, acetamido and propionamido; |
| for carboxy-(1-6C)alkyl: | carboxymethyl, 1-carboxyethyl, 2-carboxyethyl, 3-carboxypropyl and 4-carboxybutyl; |
| for (1-6C)alkoxycarbonyl-(1-6C)alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |
| for (1-6C)alkylthio: | methylthio, ethylthio and propylthio; |
| for (1-6C)alkylsulphinyl: | methylsulphinyl, ethylsulphinyl and propylsulphinyl; |
| for (1-6C)alkylsulphonyl: | methylsulphonyl, ethylsulphonyl and propylsulphonyl; |
| for N-(1-6C)allcylsulphamoyl: | N-methylsulphamoyl and N-ethylsulphamoyl; |
| for N,N-di-[(1-6C)alkyl]sulphamoyl: | N,N-dimethylsulphamoyl; |

A suitable value for a substituent on $Q_b$ when it is (3-6C)cycloalkyl is, for example, a saturated monocyclic 3- to 6-membered carbon ring such as cyclopropyl, cyclobutyl, cyclopentyl or cyclohexyl, preferably cyclopropyl, cyclopentyl or cyclohexyl, more preferably cyclopropyl.

ethyl, cyano, amino, (1-6C)alkyl, (2-6C)alkenyl, (2-6C)alkynyl, (1-6C)alkoxy, (1-6C)alkylamino, di-[(1-6C)alkyl]amino and (1-6C)alkoxycarbonyl.

$Q_a$ is heteroaryl, and $Q_a$ may optionally bear 1 or 2 substituents selected from hydroxy, halogeno, trifluoromethyl, cyano, amino, (1-6C)alkyl, (2-6C)alkenyl, (2-6C)alkynyl, (1-6C)alkoxy, (1-6C)alkylamino, di-[(1-6C)alkyl]amino and (1-6C)alkoxycarbonyl.

$Q_a$ is phenyl, pyridyl, pyrimidinyl, pyrazinyl or pyridazinyl, and $Q_a$ may optionally bear 1 or 2 substituents selected from hydroxy, halogeno, trifluoromethyl, cyano, amino, (1-6C)alkyl, (2-6C)alkenyl, (2-6C)alkynyl, (1-6C)alkoxy, (1-6C)alkylamino, di-[(1-6C)alkyl]amino and (1-6C)alkoxycarbonyl.

$Q_a$ is phenyl or heteroaryl, and $Q_a$ may optionally bear 1 or 2 substituents selected from, halogeno, (1-6C)alkyl and (1-6C)alkoxy.

$Q_a$ is phenyl, pyridyl, pyrimidinyl, pyrazinyl or pyridazinyl, and $Q_a$ may optionally bear 1 or 2 substituents selected from hydroxy, halogeno, (1-6C)alkyl and (1-6C)alkoxy.

$Q_a$ is phenyl, pyridyl, pyrimidinyl, pyrazinyl or pyridazinyl, and $Q_a$ may optionally bear 1 or 2 substituents selected from halogeno, (1-6C)alkyl and (1-6C)alkoxy.

$Q_a$ is phenyl, pyridyl or pyrimidinyl, and $Q_a$ may optionally bear 1 or 2 substituents selected from halogeno, (1-6C)alkyl and (1-6C)alkoxy.

$Q_a$ is phenyl, pyridyl, pyrimidinyl, pyrazinyl or pyridazinyl, and $Q_a$ may optionally bear 1 or 2 substituents selected from hydroxy and halogeno.

$Q_a$ is phenyl, pyridyl, pyrimidinyl, pyrazinyl or pyridazinyl, and $Q_a$ may optionally bear 1 or 2 substituents selected from hydroxy, chloro and fluoro.

$Q_a$ is phenyl, and $Q_a$ may optionally bear 1 or 2 substituents selected from hydroxy, chloro and fluoro.

$Q_a$ is phenyl, and $Q_a$ may optionally bear 1 or 2 fluoro substituents.

$Q_a$ is phenyl which optionally bears 1 or 2 substituents selected from halogeno, (1-6C)alkyl and (1-6C)alkoxy.

$Q_a$ is heteroaryl, which optionally bears 1 or 2 substituents selected from halogeno, (1-6C)alkyl and (1-6C)alkoxy.

$Q_a$ is phenyl or heteroaryl, and $Q_a$ may optionally bear 1 or 2 substituents selected from fluoro, chloro, methyl and methoxy.

$Q_a$ is phenyl, which optionally bears 1 or 2 substituents selected from fluoro, chloro, methyl and methoxy.

$Q_a$ is heteroaryl, which optionally bears 1 or 2 substituents selected from fluoro, chloro, methyl and methoxy.

$Q_a$ is phenyl, pyridyl or pyrimidinyl, which bears 1 or 2 substituents selected from fluoro, chloro, methyl and methoxy.

$Q_a$ is phenyl or heteroaryl, which bears 1 or 2 substituents selected from fluoro, chloro, methyl and methoxy.

$Q_b$ is phenyl, heteroaryl or heterocyclyl, and $Q_b$ may optionally bear 1 or 2 substituents selected from hydroxy, halogen, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl.

$Q_b$ is phenyl or heteroaryl, and $Q_b$ may optionally bear 1 or 2 substituents selected from hydroxy, halogen, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;

and wherein any of the substituents on $Q_b$ which comprise a $CH_2$ group which, is attached to 2 carbon atoms or a $CH_3$ group which is attached to a carbon atom may optionally bear on each said $CH_2$ or $CH_3$ group one or more substituents selected from hydroxy, cyano, amino, (1-6C)alkyl, (1-6C)alkoxy, (1-6C)alkylamino and di-[(1-6C)alkyl]amino.

$Q_b$ is phenyl or heteroaryl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl.

$Q_b$ is phenyl, pyridyl, pyrimidinyl, pyrazinyl, pyridazinyl, thiazolyl, thiadiazolyl, imidazolyl, isoxazolyl, oxazolyl, furanyl, thienyl, benzimidazolyl, isoquinolinyl, quinolinyl, benzothiazolyl or pyrido[1,2-a]imidazolyl, and $Q_b$ may optionally bear 1 or 2 substituents selected from hydroxy, halogen, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;

and wherein any of the substituents on $Q_b$ which comprise a $CH_2$ group which is attached to 2 carbon atoms or a $CH_3$ group which is attached to a carbon atom may optionally bear on each said $CH_2$ or $CH_3$ group one or more substituents selected from hydroxy, cyano, amino, (1-6C)alkyl, (1-6C)alkoxy, (1-6C)alkylamino and di-[(1-6C)alkyl]amino.

$Q_b$ is phenyl, pyridyl, thiazolyl, furanyl, pyrido[1,2-a]imidazolyl, thiadiazolyl, oxazolyl, isoxazolyl, piperidinyl, piperizinyl or pyrroldinyl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl.

$Q_b$ is phenyl, pyridyl, thiazolyl, furanyl, pyrido[1,2-a]imidazolyl, thiadiazolyl, oxazolyl or isoxazolyl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl.

$Q_b$ is phenyl, pyridyl, thiazolyl, furanyl, pyrido[1,2-a]imidazolyl, thiadiazolyl, oxazolyl or isoxazolyl, and $Q_b$ may optionally bear 1 or 2 substituents selected from hydroxy, fluoro, chloro, methyl, ethyl, isopropyl, methoxy, ethoxy, methoxycarbonyl and ethoxycarboyl.

$R_1$ and $R_2$ are each independently selected from hydrogen, (1-6C)alkyl, (2-6C)alkenyl and (2-6C)alkynyl;

$R_1$ and $R_2$ are each independently selected from hydrogen and (1-6C)alkyl.

$R_1$ and $R_2$ are hydrogen.

Particular novel compounds of the invention include, for example, amide derivatives of the Formula I, or pharmaceutically-acceptable salts thereof, wherein:—

(a) $Q_a$ is phenyl or heteroaryl, and $Q_a$ may optionally bear 1 or 2 substituents selected from hydroxy, halogeno, trifluoromethyl, cyano, amino, (1-6C)alkyl, (2-6C)alkenyl, (2-6C)alkynyl, (1-6C)alkoxy, (1-6C)alkylamino, di-[(1-6C)alkyl]amino and (1-6C)alkoxycarbonyl;

$Q_b$ is phenyl, heteroaryl or heterocyclyl, and $Q_b$ may optionally bear 1 or 2 substituents selected from hydroxy, halogen, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl and $R_1$ and $R_2$ are hydrogen.

(b) $Q_a$ is phenyl, pyridyl, pyrimidinyl, pyrazinyl or pyridazinyl, and $Q_a$ may optionally bear 1 or 2 substituents selected from hydroxy, halogeno, trifluoromethyl, cyano, amino, (1-6C)alkyl, (2-6C)alkenyl, (2-6C)alkynyl, (1-6C)alkoxy, (1-6C)alkylamino, di-[(1-6C)alkyl]amino and (1-6C)alkoxycarbonyl;

$Q_b$ is phenyl, pyridyl, thiazolyl, furanyl, pyrido[1,2-a]imidazolyl, thiadiazolyl, oxazolyl, isoxazolyl, piperidinyl, piperizinyl or pyrroldinyl, and $Q_b$ may optionally bear 1 or 2 substituents selected from hydroxy, halogen, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl and $R_1$ and $R_2$ are hydrogen.

(c) $Q_a$ is phenyl which optionally bears 1 or 2 substituents selected from, halogeno, (1-6C)alkyl and (1-6C)alkoxy; $Q_b$ is phenyl, pyridyl, thiazolyl, furanyl, Pyrido[1,2-a]imidazolyl, thiadiazolyl, oxazolyl or isoxazolyl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl and $R_1$ and $R_2$ are hydrogen.

(d) $Q_a$ is phenyl, which optionally bears 1 or 2 substituents selected from, fluoro, chloro, methyl and methoxy; $Q_b$ is phenyl, pyridyl, thiazolyl, furanyl, pyrido[1,2-a]imidazolyl, thiadiazolyl, oxazolyl or isoxazolyl, and $Q_b$ may optionally bear 1 or 2 substituents selected from hydroxy, fluoro, chloro, methyl, ethyl, isopropyl, methoxy, ethoxy, methoxycarbonyl and ethoxycarbonyl and $R_1$ and $R_2$ are hydrogen.

A particular preferred compound of the invention is, for example:—

3-{[4-(benzyloxy)benzoyl]amino}-N-cyclopropyl-4-methylbenzamide;

3-{[3-(benzyloxy)benzoyl]amino}-N-cyclopropyl-4-methylbenzamide;

4-(benzyloxy)-N-{5-[(cyclopropylamino)carbonyl]-2-methylphenyl}-3-methylbenzamide;

4-(benzyloxy)-3-fluoro-N-{5-[(cyclopropylamino)carbonyl]-2-methylphenyl}benzamide;

4-(benzyloxy)-3-chloro-N-{5-[(cyclopropylamino)carbonyl]-2-methylphenyl}benzamide;

N-cyclopropyl-4-methyl-3-{[4-(pyridin-2-ylmethoxy)benzoyl]amino}benzamide;

N-cyclopropyl-4-methyl-3-{[4-(1,3-thiazol-4-ylmethoxy)benzoyl]amino}benzamide;

N-cyclopropyl-4-methyl-3-{[4-(pyridin-3-ylmethoxy)benzoyl]amino}benzamide;

N-cyclopropyl-4-methyl-3-{4-[(5-methyl isoxazol-3-yl)methoxy]benzoyl}amino)benzamide;

3-({4-[(5-chloro-1,2,3-thiadiazol-4-yl)methoxy]benzoyl}amino)-N-cyclopropyl-4-methylbenzamide;

N-cyclopropyl-3-{[4-(imidazo[1,2-a]pyridin-2-ylmethoxy)benzoyl]amino}-4-methylbenzamide;

N-cyclopropyl-4-methyl-3-({4-[(2-methyl-1,3-thiazol-4-yl)methoxy]benzoyl}amino)benzamide;

N-cyclopropyl-3-({4-[(3,5-dimethylisoxazol-4-yl)methoxy]benzoyl}amino)-4-methylbenzamide;

N-cyclopropyl-4-methyl-3-{[4-(1,2,5-thiadiazol-3-ylmethoxy)benzoyl]amino}benzamide;

methyl 5-({-4-[({5-[(cyclopropylamino)carbonyl]-2-methylphenyl}amino)carbonyl]phenoxy}methyl)-2-furoate;

3-({4-[(2-chloro-1,3-thiazol-5-yl)methoxy]benzoyl}amino)-N-cyclopropyl-4-methylbenzamide;

4-(benzyloxy)-N-{5-[(cyclopropylamino)carbonyl]-2-methylphenyl}-3-methoxybenzamide;

N-{5-[(cyclopropylamino)carbonyl]-2-methylphenyl}-3-methoxy-4-(pyridin-2-ylmethoxy)benzamide;

N-{5-[(cyclopropylamino)carbonyl]-2-methylphenyl}-3-methoxy-4-(1,3-thiazol-4-ylmethoxy)benzamide;

N-cyclopropyl-4-methyl-3-{[3-methyl-4-(pyridin-2-ylmethoxy)benzoyl]amino}benzamide;

N-cyclopropyl-4-methyl-3-{[3-methyl-4-(1,3-thiazol-4-ylmethoxy)benzoyl]amino}benzamide;

N-{5-[(cyclopropylamino)carbonyl]-2-methylphenyl}-3-fluoro-4-(pyridin-2-ylmethoxy)benzamide;

N-{5-[(cyclopropylamino)carbonyl]-2-methylphenyl}-3-fluoro-4-[(2-methyl-1,3-thiazol-4-yl)methoxy]benzamide;

N-{5-[(cyclopropylamino)carbonyl]-2-methylphenyl}-4-[(3,5-dimethylisoxazol-4-yl)methoxy]-3-fluorobenzamide;

N-{5-[(cyclopropylamino)carbonyl]-2-methylphenyl}-3-fluoro-4-(1,2,5-thiadiazol-3-ylmethoxy)benzamide;

N-cyclopropyl-4-methyl-3-{[3-(1,3-thiazol-4-ylmethoxy)benzoyl]amino}benzamide;

N-cyclopropyl-4-methyl-3-({3-[(2-methyl-1,3-thiazol-4-yl)methoxy]benzoyl}amino)benzamide;

N-cyclopropyl-4-methyl-3-{[3-(pyridin-2-ylmethoxy)benzoyl]amino}benzamide;
N-{5-[(cyclopropylamino)carbonyl]-2-methylphenyl}-3-fluoro-4-(1,3-thiazol-4-ylmethoxy)benzamide;
N-cyclopropyl-4-methyl-3-({3-methyl-4-[(2-methyl-1,3-thiazol-4-yl)methoxy]benzoyl}amino)benzamide;
N-{5-[(cyclopropylamino)carbonyl]-2-methylphenyl}-4-[(3,5-dimethylisoxazol-4-yl)methoxy]-3-methylbenzamide;
N-cyclopropyl-4-methyl-3-{[3-methyl-4-(1,2,5-thiadiazol-3-ylmethoxy)benzoyl]amino}benzamide;
methyl 5-({4-[({5-[(cyclopropylamino)carbonyl]-2-methylphenyl}amino)carbonyl]-2-methylphenoxy}methyl)-2-furoate;
3-chloro-N-{5-[(cyclopropylamino)carbonyl]-2-methylphenyl}-4-(pyridin-2-ylmethoxy)benzamide;
3-chloro-N-{5-[(cyclopropylamino)carbonyl]-2-methylphenyl}-4-(1,3-thiazol-4-ylmethoxy)benzamide;
N-cyclopropyl-3-({3-[(3,5-dimethylisoxazol-4-yl)methoxy]benzoyl}amino)-4-methylbenzamide;
N-cyclopropyl-4-methyl-3-{[3-(1,2,5-thiadiazol-3-ylmethoxy)benzoyl]amino}benzamide;
3-({3-[(2-chloro-1,3-thiazol-5-yl)methoxy]benzoyl}amino)-N-cyclopropyl-4-methylbenzamide;
N-{5-[(cyclopropylamino)carbonyl]-2-methyl-phenyl}-3-fluoro-4-(imidazo[1,2-a]pyridin-2-ylmethoxy)benzamide;
N-cyclopropyl-3-({4-[(4-methoxypyridin-2-yl)methoxy]benzoyl}amino)-4-methylbenzamide;
N-cyclopropyl-4-methyl-3-{[4-(1-pyridin-2-ylethoxy)benzoyl]amino}benzamide;
N-cyclopropyl-3-({3-[(4-methoxypyridin-2-yl)methoxy]benzoyl}amino)-4-methylbenzamide;
N-cyclopropyl-3-[(4-{[5-(hydroxymethyl)pyridin-2-yl]methoxy}benzoyl)amino]-4-methylbenzamide;
N-cyclopropyl-3-[(4-{[5-(1-hydroxy-1-methylethyl)pyridin-2-yl]methoxy}benzoyl)amino]-4-methylbenzamide;
N-cyclopropyl-3-{[4-({5-[(isopropylamino)methyl]pyridin-2-yl}methoxy)benzoyl]amino}-4-methylbenzamide;
N-cyclopropyl-3-{[4-({5-[(dimethylamino)methyl]pyridin-2-yl}methoxy)benzoyl]amino}-4-methylbenzamide;
methyl 6-({4-[({5-[(cyclopropylamino)carbonyl]-2-methylphenyl}amino)carbonyl]phenoxy}methyl)nicotinate;
N-cyclopropyl-3-{[4-({5-[2-(dimethylamino)ethoxy]pyridin-2-yl}methoxy)benzoyl]amino}-4-methylbenzamide;
N-cyclopropyl-3-[(4-{[5-(1,3-dioxolan-2-ylmethoxy)pyridin-2-yl]methoxy}benzoyl)amino]-4-methylbenzamide;
N-cyclopropyl-3-({4-[(5-hydroxypyridin-2-yl)methoxy]benzoyl}amino)-4-methylbenzamide
methyl 6-({4-[({5-[(cyclopropylamino)carbonyl]-2-methylphenyl}amino)carbonyl]phenoxy}methyl)pyridine-2-carboxylate;
N-cyclopropyl-3-[(4-{[6-(hydroxymethyl)pyridin-2-yl]methoxy}benzoyl)amino]-4-methylbenzamide;
N-cyclopropyl-3-[(4-{[6-(1-hydroxy-1-methylethyl)pyridin-2-yl]methoxy}benzoyl)amino]-4-methylbenzamide;
N-cyclopropyl-3-({4-[(6-{[2-(diethylamino)ethoxy]methyl}pyridin-2-yl)methoxy]benzoyl}amino)-4-methylbenzamide;
N-cyclopropyl-3-({4-[(6-{[2-(dimethylamino)ethoxy]methyl}pyridin-2-yl)methoxy]benzoyl}amino)-4-methylbenzamide;
N-cyclopropyl-4-methyl-3-({4-[(1-oxidopyridin-2-yl)methoxy]benzoyl}amino)benzamide;
N-{5-[(cyclopropylamino)carbonyl]-2-methylphenyl}-2-(imidazo[1,2-a]pyridin-2-ylmethoxy)pyrimidine-5-carboxamide;
N-{5-[(cyclopropylamino)carbonyl]-2-methylphenyl}-2-(1,3-thiazol-2-ylmethoxy)pyrimidine-5-carboxamide;
N-{5-[(cyclopropylamino)carbonyl]-2-methylphenyl}-2-(pyrimidin-2-ylmethoxy)pyrimidine-5-carboxamide;
{5-[(cyclopropylamino)carbonyl]-2-methylphenyl}-2-[(1-methyl-1H-imidazol-2-yl)methoxy]pyrimidine-5-carboxamide;
N-{5-[(cyclopropylamino)carbonyl]-2-methylphenyl}-2-[(1,5-dimethyl-1H-pyrazol-3-yl)methoxy]pyrimidine-5-carboxamide;
N-{5-[(cyclopropylamino)carbonyl]-2-methylphenyl}-2-[(1,3-dimethyl-1H-pyrazol-5-yl)methoxy]pyrimidine-5-carboxamide;
N-{5-[(cyclopropylamino)carbonyl]-2-methylphenyl}-2-[(3-methylpyridin-2-yl)methoxy]pyrimidine-5-carboxamide;
N-{5-[(cyclopropylamino)carbonyl]-2-methylphenyl}-2-[(1-methyl-1H-benzimidazol-2-yl)methoxy]pyrimidine-5-carboxamide;
{5-[(cyclopropylamino)carbonyl]-2-methylphenyl}-2-(isoquinolin-1-ylmethoxy)pyrimidine-5-carboxamide;
N-{5-[(cyclopropylamino)carbonyl]-2-methylphenyl}-2-(quinolin-2-ylmethoxy)pyrimidine-5-carboxamide;
2-(1,3-benzothiazol-2-ylmethoxy)-N-{5-[(cyclopropylamino)carbonyl]-2-methylphenyl}pyrimidine-5-carboxamide;
N-{5-[(cyclopropylamino)carbonyl]-2-methylphenyl}-pyridin-2-ylethoxy)pyrimidine-5-carboxamide;
N-{5-[(cyclopropylamino)carbonyl]-2-methylphenyl}-2-(1,3-thiazol-4-ylmethoxy)pyrimidine-5-carboxamide;
{5-[(cyclopropylamino)carbonyl]-2-methylphenyl}-2-(pyridin-2-ylmethoxy)pyrimidine-5-carboxamide;
N-cyclopropyl-3-({4-[(5-cyclopropyl-1,3,4-thiadiazol-2-yl)methoxy]benzoyl}amino)-4-methylbenzamide;
{5-[(cyclopropylamino)carbonyl]-2-methylphenyl}-6-(pyridin-2-ylmethoxy)nicotinamide;
{5-[(cyclopropylamino)carbonyl]-2-methylphenyl}-5-(pyridin-2-ylmethoxy)pyrazine-2-carboxamide;
3-({4-[(6-bromopyridin-2-yl)methoxy]benzoyl}amino)-N-cyclopropyl-4-methylbenzamide
N-{5-[(cyclopropylamino)carbonyl]-2-methylphenyl}-3,5-difluoro-4-(pyridin-2-ylmethoxy)benzamide;
N-cyclopropyl-4-methyl-3-({4-[(6-methylpyridin-2-yl)methoxy]benzoyl}amino)benzamide;
N-cyclopropyl-4-methyl-3-({4-[(3-methylpyridin-2-yl)methoxy]benzoyl}amino)benzamide;
N-cyclopropyl-4-methyl-3-{[4-(pyrimidin-2-ylmethoxy)benzoyl]amino}benzamide;
N-cyclopropyl-4-methyl-3-{[4-(pyridazin-3-ylmethoxy)benzoyl]amino}benzamide;
N-cyclopropyl-3-{[4-({6-[(2-methoxyethyl)amino]pyridin-2-yl}methoxy)benzoyl]amino}-4-methylbenzamide;
N-cyclopropyl-3-({4-[(6-{[2-(dimethylamino)ethyl]amino}pyridin-2-yl)methoxy]benzoyl}amino)-4-methylbenzamide;
5-(benzyloxy)-N-{5-[(cyclopropylamino)carbonyl]-2-methylphenyl}pyridine-2-carboxamide
N-{5-[(cyclopropylamino)carbonyl]-2-methylphenyl}-5-(pyridin-2-ylmethoxy)pyridine-2-carboxamide; and
N-cyclopropyl-4-methyl-3-[(4-{[4-(methylsulfonyl)benzyl]oxy}benzoyl)amino]benzamide;
or a pharmaceutically-acceptable salt thereof.

Compounds of the Formula I, or a pharmaceutically-acceptable salts thereof, may be prepared by any process known to be applicable to the preparation of chemically-related compounds. Suitable processes are illustrated by, for example, those in WO 00/07980. Such processes, when used to prepare a novel compound of the Formula I are provided as a further feature of the invention and are illustrated by the following representative process variants in which, unless otherwise stated, $Q_a$, $Q_b$, $R_1$ and $R_2$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt thereof, may be prepared by reacting a benzoic acid of the Formula II, or a activated derivative thereof,

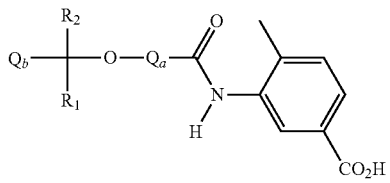

II with an amine of the Formula III

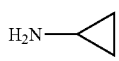

III under standard amide bond forming conditions, wherein $Q_a$, $Q_b$, $R_1$ and $R_2$ are as defined hereinbefore and wherein any functional group is optionally protected, and:

(i) removing any protecting groups; and
(ii) optionally forming a pharmaceutically-acceptable salt.

A suitable activated derivative of an acid of the Formula II is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, −78 to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl)silyl groups (for example trimethylsilyl and tert-butyldimethylsilyl); tri(lower allyl)silyl lower alkyl groups (for example trimethylsilylethyl); and (2-6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; trialkylsilyl (for example trimethylsilyl and tert-butyldimethylsilyl); allylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 3rd Edition, by Green and Wuts, published by John Wiley & Sons for general guidance on protecting groups.

The benzoic acid of Formula II may be prepared by the cleavage of the corresponding ester thereof which, in turn, may be prepared by reaction of an acid of Formula IV wherein $Q_a$, $Q_b$, $R_1$ and $R_2$ are as defined hereinbefore, or an activated derivative thereof as defined hereinbefore,

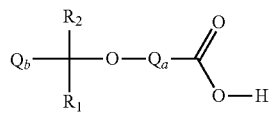

IV with an aniline of Formula V

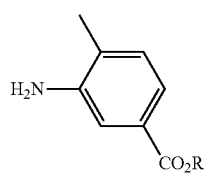

V wherein R is, for example, lower alkyl or benzyl, under suitable amide bond forming conditions as defined hereinbefore.

Typical conditions include activating the carboxy group of the compound of Formula IV, for example by treatment with a halo reagent (for example oxalyl chloride) to form an acyl halide in an organic solvent at ambient temperature and then reacting the activated compound with the aniline of Formula V. Any functional groups are protected and deprotected as necessary.

(b) A compound of the Formula I, or a pharmaceutically-acceptable salt thereof, may be prepared by reacting an acid of the Formula N, or an activated derivative thereof as defined hereinbefore,

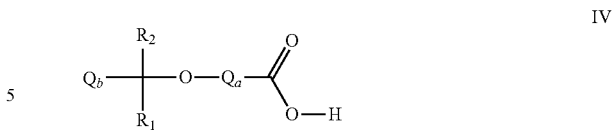

IV with an aniline of the Formula VI

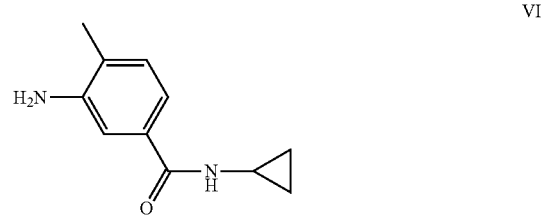

VI under standard amide bond forming conditions as defined hereinbefore, wherein $Q_a$, $Q_b$, $R_1$ and $R_2$ are as defined hereinbefore and wherein any functional group is optionally protected, and:

(i) removing any protecting groups;
(ii) optionally forming a pharmaceutically-acceptable salt.

The aniline of Formula VI may be prepared by reduction of the corresponding nitro compound using convention procedures such as those illustrated in the Examples. Typical reaction conditions include the use of ammonium formate or hydrogen gas in the presence of a catalyst (for example palladium-on-carbon) in the presence of an organic solvent (preferably a polar protic solvent), preferably with heating, for example to about 60° C. Any functional groups are protected and deprotected as necessary.

(c) A compound of the Formula I wherein a substituent on $Q_a$ or $Q_b$ is (1-6C)alkoxy or substituted (1-6C)alkoxy, (1-6C)alkylamino, di-[(1-6C)alkyl]amino or substituted (1-6C)alkylamino, may be prepared by the alkylation, conveniently in the presence of a suitable base as defined hereinbefore, of an amide derivative of the Formula I wherein a substituent on $Q_a$ or $Q_b$ is hydroxy or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, or for the alkylation of hydroxy to heterocyclyloxy, for example an alkyl or substituted alkyl halide, for example a (1-6C)alkyl chloride, bromide or iodide or a substituted (1-6C)alkyl chloride, bromide or iodide or a heterocyclyl chloride, bromide or iodide, in the presence of a suitable base as defined hereinbefore.

(d) A compound of the Formula I wherein a substituent on $Q_a$ or $Q_b$ is (1-6C)alkanoylamino or substituted (2-6C)alkanoylamino may be prepared by the acylation of a compound of the Formula I wherein a substituent on $Q_a$ or $Q_b$ is amino.

A suitable acylating agent is, for example, any agent known in the art for the acylation of amino to acylamino, for example an acyl halide, for example a (1-6C)alkanoyl chloride or bromide, conveniently in the presence of a suitable base, as defined hereinbefore, an alkanoic acid anhydride or mixed anhydride, for example a (1-6C)alkanoic acid anhydride such as acetic anhydride or the mixed anhydride formed by the reaction of an alkanoic acid and a (1-6C)alkoxycarbonyl halide, for example a (1-6C)alkoxycarbonyl chloride, in the presence of a suitable base as defined hereinbefore. In general the acylation is carried out in a suitable inert solvent or diluent as defined hereinbefore and at a temperature, in the range, for example, −30 to 120° C., conveniently at or near ambient temperature.

(e) A compound of the Formula I wherein a substituent on $Q_b$ is (1-6C)alkanesulphonylamino may be prepared by the reaction of a compound of the Formula I wherein a substituent on $Q_b$ is amino with a (1-6C)alkanesulphonic acid, or an activated derivative thereof.

A suitable activated derivative of a (1-6C)alkanesulphonic acid is, for example, an alkanesulphonyl halide, for example an alkanesulphonyl chloride formed by the reaction of the sulphonic acid and an inorganic acid chloride, for example thionyl chloride. The reaction is preferably carried out in the presence of a suitable base as defined hereinbefore, particularly pyridine, and in a suitable inert solvent or diluent as defined hereinbefore, particularly methylene chloride.

(f) A compound of the Formula I wherein a substituent on $Q_a$ or $Q_b$ is amino-(1-6C)alkyl, (1-6C)alkylamino-(1-6C)alkyl, di-[(1-6C)alkyl]amino-(1-6C)alkyl, may be prepared by the reaction of a compound of the Formula I wherein a substituent on $Q_b$ is a group of the formula -(1-6C)alkylene-Z wherein Z is a displaceable group with an appropriate amine.

A suitable displaceable group Z is, for example, a halogen group such as fluoro, chloro or bromo, a (1-6C)alkanesulphonyloxy group such as methanesulphonyloxy or an arylsulphonyloxy group such as 4-toluenesulphonyloxy.

The reaction is conveniently carried out in the presence of a suitable base as defined hereinbefore and in the presence of a suitable inert diluent or carrier as defined hereinbefore. The reaction is conveniently carried out at a temperature in the range 10 to 150° C., preferably at or near 50° C.

(g) A compound of the Formula I wherein a substituent on $Q_a$ or $Q_b$ is an amino group may be prepared by the reduction of a compound of the Formula I wherein a substituent on $Q_a$ or $Q_b$ is a nitro group.

Typical reaction conditions include the use of ammonium formate or hydrogen gas in the presence of a catalyst, for example a metallic catalyst such as palladium-on-carbon. Alternatively a dissolving metal reduction may be carried out; for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating, for example to about 60° C. Any functional groups are protected and deprotected as necessary.

The following biological assays and Examples serve to illustrate the present invention.

Biological Assays

The following assays can be used to measure the p38 kinase-inhibitory, the TNF-inhibitory and anti-arthritic effects of compounds of the Formula I:

In Vitro Enzyme Assay

The ability test compounds to inhibit the enzyme p38 kinase was assessed. Activity of the test compound against each of the p38α and p38II isoforms of the enzyme was determined.

Human recombinant MKK6 (GenBank Accession Number G1209672) was isolated from Image clone 45578 (*Genomics*, 1996, 33, 151) and utilised to produce protein in the form of a GST fusion protein in a pGEX vector using analogous procedures to those disclosed by J. Han et al., *Journal of Biological Chemistry*, 1996, 271, 2886-2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta*, 1995, 1265, 224-227 and Y. Jiang et al., *Journal of Biological Chemistry*, 1996, 271, 17920-17926.

Both p38 protein isoforms were expressed in *E. coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated *E. coli*-expressed MKK6 retained sufficient activity to fully activate both isoforms of p38. For p38α, the activation incubate comprised p38α (50 μl of 10 mg/ml), MKK6 (5 μl of 12 mg/ml), 'Kinase buffer' [550 μl; pH 7.4 buffer comprising Tris HCl (50 mM), EGTA (0.1 mM), sodium orthovanadate (0.1 mM) and (1-mercaptoethanol (0.1%)], Mg [75 μl of 100 mM Mg(OCOCH$_3$)$_2$] and ATP (75 μl of 1 mM). The activation incubate for p38β was similar to the above except containing p38β enzyme (82 μl at 3.05 mg/ml) and 518 μl "Kinase buffer". p38α and p38β activation incubates were either used fresh or aliquoted and stored at −80° C.

The test compound was solubilised in DMSO (10 mM) and 1:3 serial dilutions in DMSO carried out in polypropylene plates (Costar 3365). Compound dilutions were then diluted 1:10 in "Kinase buffer" and 10 μl transferred to a microtiter assay plate (Costar 3596). Control wells contained 10 μl (1:10 dilution in kinase buffer) DMSO. 'Kinase Assay Mix' [301.1.1; comprising Myelin Basic Protein (Sigma M-1891; 0.5 ml of a 6.66 mg/ml solution in "Kinase buffer"), activated p38α enzyme (3.8 μl) and 'Kinase Buffer' (2.55 ml)] was then added. Control wells on each plate either contained the above "Kinase Assay Mix" (n=6 replicates) or contained "Kinase Assay Mix" in which the activated p38 enzyme was replaced by Kinase buffer (n=6 replicates). 'Labelled ATP' was then added to all wells DOW; comprising 50 μM ATP, 5 μCi $^{33}$P ATP (Amersham International cat. no. AH9968) and 50 mM Mg(OCOCH$_3$)$_2$]. For p38β, 23 μl activated p38β enzyme and "Kinase buffer" (2.53 ml) were included in the "Kinase Assay Mix". The final concentration of test compound was 2.4 μM-0.001 μM (n=2 replicates). Microtiter plates were incubated at ambient temperature (with gentle agitation) for 60 minutes and the reaction stopped by addition of 20% trichloroacetic acid (TCA) (50 μl). The precipitate protein was captured onto filter plates (PerkinElmer 6005174) using a Packard Filtermate harvester (2% TCA wash) which was then dried overnight and 25 μl MICROSCINT O (Packard O6013611) added to each well. Plates were counted on a Top Count scintillation counter. Dose response curves were generated using an in house automated data analysis package and an Origin curve fitting package.

In Vitro Cell-Based Assays (i) PBMC

The ability of a test compound to inhibit TNFα production was assessed by using human peripheral blood mononuclear cells which synthesise and secrete TNFα when stimulated with lipopolysaccharide (LPS).

Peripheral blood mononuclear cells (PBMC) were isolated from heparinised (10 units/ml heparin) human blood by density centrifugation (Lymphoprep™; Nycomed). Mononuclear cells were resuspended in "Culture Medium" [RPMI 1640 medium (Sigma R0883) containing 50 units/ml penicillin, 50 µg/ml streptomycin and 2 mM glutamine] supplemented with 1% heat-inactivated human AB serum (Sigma H-1513)]. Compounds were solubilised in DMSO at a concentration of 20 mM, diluted 1:100 in "culture medium" and serial dilutions carried out in "Culture Medium" containing 1% DMSO. PBMCs ($2.2 \times 10^5$ cells in 160 µl culture medium) were incubated with 20 µl of varying concentrations of test compound (duplicate cultures) or 20 µl culture medium containing 1% DMSO (control wells) for 30 minutes at 37° C. in a humidified (5% $CO_2$/95% air) incubator (Corning 3595; 96 well flat-bottom tissue culture plates). 20 µl lipopolysaccharide [LPS E. Coli 0111:B4 (Sigma L-4130), final concentration 0.1 µg/ml] solubilised in "Culture Medium" was added to appropriate wells. 20 µl Culture Medium was added to "medium alone" control wells. Six "LPS alone" and six "medium alone" controls were included on each 96 well plate.

The test compound was tested for TNFα inhibitory activity over a final concentration dose range of 20 µM-0.0001 µM. Each test included a known TNFα inhibitor i.e. the p38 MAPK inhibitor, SB203580 (Lee, J. C., et al (1994) Nature 372 p739-746). Plates were incubated for 24 hours at 37° C. (humidified incubator) after which 100 µl of the supernatant was removed from each well and stored at −80° C. (96 well round-bottom plates; Corning 3799). TNFα levels were determined in each sample using a human TNFα ELISA (using R&D Systems paired antibodies, MAB610 and BAF210.

$$\% \text{ inhibition} = \frac{(LPS \text{ alone} - \text{medium alone}) - (\text{test concentration} - \text{medium alone})}{(LPS \text{ alone} - \text{medium alone})} \times 100$$

(ii) Human Whole Blood

The ability of a test compound to inhibit TNFα production was also assessed in a human whole blood assay. Human whole blood secretes TNFα when stimulated with LPS.

Heparinised (10 units/ml) human blood was obtained from volunteers. 160 µl whole blood was added to 96 well round-bottom plates (Corning 3799). Compounds were solubilised in DMSO at a concentration of 10 mM, diluted 1:100 in "culture medium" [RPMI 1640 medium (Sigma) containing 50 units/ml penicillin, 50 µg/ml streptomycin and 2 mM glutamine] and subsequently serial dilutions were made in culture medium containing 1% DMSO. 20 µl of each test concentration was added to appropriate wells (triplicate cultures)(final concentration dose range of 10 µM-0.0001 µM). 20 µl of RPMI culture medium containing 1% DMSO was added to control wells.

Plates were incubated for 30 minutes at 37° C. (humidified incubator), prior to addition of 20 µl LPS (final concentration 10 µg/ml). Culture medium was added to control wells. Six "LPS alone" and six "medium alone" controls were included in each test. Plates were incubated for 6 hours at 37° C. (humidified incubator). Plates were centrifuged (2000 rpm for 10 minutes) and 80 µl plasma removed and stored at −80° C. (Corning 3799 plates). TNFα levels were measured by ELISA using paired antibodies from R&D Systems (catalogue nos. MAB610 and BAF210).

In Vivo Assessment

The ability of a test compound to inhibit TNFα synthesis in vivo was assessed in a rat lipopolysaccharide (LPS)-challenge model. Briefly, compound was dosed orally (100-0.3 mg/kg in 20% DMSO (Sigma D-2650)/60% PEG 400 (Fisher Scientific P/3676/08)/20% sterile de-ionised water; 5 animals per group) to female Wistar Alderley Park (AP) rats (80-100 g) at appropriate timepoints prior to challenge with LPS. Control animals (10 per group) were dosed vehicle alone. LPS (LPS E. Coli 0111:B4; Sigma L-4130) was administered intravenously (30 µg in 0.2 ml sterile physiological saline (Phoenix Pharma Ltd). A control group were challenged with 0.2 ml sterile physiological saline. Blood was obtained 60 minutes later from anaesthetised animals and serum isolated after 2 hours incubation at ambient temperature (Sarstedt serum separator 1 ml microtubes, ref 41.1500.005) and centrifugation. Serum samples were stored at −80° C. prior to determination of TNFα content by ELISA (R&D Systems rat TNFα Quantikine kit, catalogue no. SRTA00). % inhibition TNFα calculated as 100−[(compound treated−saline control)/LPS control−saline control)×100]

Test as Anti-Arthritic Agent

Compound was tested for activity in a rat streptococcal cell-wall-induced arthritis model (SCW) [for further information see Carlson, R. P. and Jacobsen, P. B. (1999) Comparison of adjuvant and streptococcal cell-wall-induced arthritis in the rat. In In Vivo Models of Inflammation, eds Morgan, D. W. and Marshall, L. A., Birkhauser Verlag, Basel, Switzerland].

Briefly, female Lewis rats (160-180 g) were sensitised by intra-articular injection of 5 µg streptococcal cell wall (Lee Labs, PG-PS 100P) in 20 µl sterile physiological saline into the left ankle. Responsiveness was assessed 3 days later and animals randomised. Arthritis was induced 21 days after sensitisation (designated day 0) by intravenous injection of 100 µg scw (in 500 µl sterile physiological saline). Compound was dosed orally (50-1 mg/kg once daily) (4 ml/kg) either before (day-1) or after disease onset (day+1) (10 animals per test group; vehicle 0.5% (w/v) HPMC and 0.1% (w/v) polysorbate 80). Control animals (n=10) received vehicle alone. "Non-induced" control animals which were dosed with vehicle were also included (5 animals per group). Animals were weighed on a daily basis from day-1 and ankle diameters measured with Vernier callipers on a daily basis from day-1. At termination on day 6, left hind limbs were removed and fixed in 10% formalin for histological assessment.

Although the pharmacological properties of the compounds of the Formula I vary with structural change as expected, in general a compound of the Formula a gives over 50% inhibition of p38α and/or p38β at concentrations less than 1 µM. No physiologically unacceptable toxicity was observed at the effective dose for compounds tested of the present invention.

The following table shows $IC_{50}$ figures for a representative selection of compounds according to the invention, as well as for the Comparator Compound X disclosed in WO 00/07980 when tested in the above assays:

| Example | p38α (μM) | Human Whole Blood (μM) |
|---|---|---|
| Comparator Compound X | 4.4 | >10 |
| 5[ac] | 0.007 | 0.07 |
| 5[e] | 0.01 | 0.52 |
| 5[y] | 0.006 | 0.14 |
| 5[z] | 0.007 | 0.30 |
| 8 | 0.059 | 1.8 |
| 23[a] | 0.17 | 1.7 |

According to a further aspect of the invention there is provided a pharmaceutical composition which comprises compound of the Formula I, or a pharmaceutically-acceptable salt thereof, in association with a pharmaceutically-acceptable diluent or carrier.

According to a further aspect of the invention there is provided a pharmaceutical composition for use in the treatment of diseases mediated by cytokines which comprises compound of the Formula I, or a pharmaceutically-acceptable salt thereof, in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I of the invention will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided a compound of the Formula I, or a pharmaceutically-acceptable salt thereof, for use in a method of treatment of the human or animal body by therapy.

According to a further aspect of the invention there is provided the use of a compound of the Formula I, or a pharmaceutically-acceptable salt thereof, in the manufacture of a medicament.

According to a further aspect of the invention there is provided the use of a compound of the Formula I, or a pharmaceutically-acceptable salt thereof, in the manufacture of a medicament for use in the treatment of medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt thereof.

In a further aspect the present invention provides a method of treating a disease or medical condition mediated by cytokines which comprises administering to a warm-blooded animal in need thereof a cytokine inhibiting amount of a compound of the Formula I, or a pharmaceutically-acceptable salt thereof.

In a further aspect the present invention provides a method of treating a disease or medical condition mediated by the production or effect of cytokines which comprises administering to a warm-blooded animal in need thereof a cytokine inhibiting amount of a compound of the Formula I, or a pharmaceutically-acceptable salt thereof.

In a further aspect on the invention there is provided a method for inhibiting the production or effect of a cytokine in a warm-blooded animal in need thereof a p38 kinase inhibiting amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt thereof.

In a further aspect the present invention provides a compound of the Formula I, or a pharmaceutically-acceptable salt thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt thereof.

In a further aspect the present invention provides the use of a compound of the Formula I, or a pharmaceutically-acceptable salt thereof, in the manufacture of a medicament for use in the treatment of rheumatoid arthritis, asthma, chronic obstructive pulmonary disease, inflammatory bowel disease, multiple sclerosis, AIDS, septic shock, congestive heart failure, ischaemic heart disease or psoriasis.

In a further aspect the present invention provides a method of treating rheumatoid arthritis, asthma, chronic obstructive pulmonary disease, inflammatory bowel disease, multiple sclerosis, AIDS, septic shock, congestive heart failure, ischaemic heart disease or psoriasis which comprises administering to a warm-blooded animal an effective amount of a compound of the Formula I, or a pharmaceutically-acceptable salt thereof.

A compound of the Formula I may be used in combination with other drugs and therapies used in the treatment of disease states which would benefit from the inhibition of cytokines, in particular TNF and IL-1. For example, a compound of the Formula I could be used in combination with drugs and therapies used in the treatment of rheumatoid arthritis, asthma, chronic obstructive pulmonary disease, inflammatory bowel disease, multiple sclerosis, AIDS, septic shock, congestive heart failure, ischaemic heart disease, psoriasis and the other disease states mentioned earlier in this specification.

For example, by virtue of its ability to inhibit cytokines, a compound of the Formula I is of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I of the present invention with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

A compound of the Formula I may also be used with anti-inflammatory agents such as an inhibitor of the enzyme 5-lipoxygenase.

A compound of the Formula I may also be used in the treatment of conditions such as rheumatoid arthritis in combination with antiarthritic agents such as gold, methotrexate, steroids and pencillinamine, and in conditions such as osteoarthritis in combination with steroids.

A compound of the Formula I may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

A compound of the Formula I may be used in the treatment of asthma in combination with antiasthmatic agents such as steroids, bronchodilators and leukotriene antagonists.

In particular, for the treatment of the inflammatory diseases rheumatoid arthritis, psoriasis, inflammatory bowel disease, chronic obstructive pulmonary disease, asthma and allergic rhinitis a compound of the present invention may be combined with agents such as TNF-$\alpha$ inhibitors such as anti-TNF monoclonal antibodies (such as Remicade, CDP-870 and $D_2E_7$.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefimomide; ciclesonide; hydroxychloroquine, d-penicillamine, auranofin or parenteral or oral gold.

The present invention still further relates to the combination of a compound of the Formula I together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the Formula I together with a receptor antagonist for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralulcast (CGP 45715A), and BAY x 7195.

The present invention still further relates to the combination of a compound of the Formula I together with a PDE4 inhibitor including inhibitors of the isoform PDE4D.

The present invention still further relates to the combination of a compound of the Formula I together with a antihistaminic H.sub1. receptor antagonists such as cetirizine, loratadine, desloratadine, fexofenadine, astemizole, azelastine, and chlorpheniramine.

The present invention still further relates to the combination of a compound of the Formula I together with a gastroprotective H.sub2. receptor antagonist.

The present invention still further relates to the combination of a compound of the Formula I together with an α.sub1.- and α.sub2.-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the Formula I together with anticholinergic agents such as ipratropium bromide; tiotropium bromide; oxitropium bromide; pirenzepine; and telenzepine.

The present invention still further relates to the combination of a compound of the Formula I together with a β.sub1.- to β.sub4.-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the Formula I together with an insulin-like growth factor type I (IGF-1) mimetic.

The present invention still further relates to the combination of a compound of the Formula I together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the Formula I together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of a compound of the Formula I together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of a compound of the Formula I together with antiviral agents such as Viracept, AZT, aciclovir and famciclovir, and antisepsis compounds such as Valant.

The present invention still further relates to the combination of a compound of the Formula I together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the Formula I together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the Formula I together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-B.sub 1.- and B.sub2.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin NK.sub1. and NK.sub3. receptor antagonists selected from the group consisting of NKP-608C; SB-233412 (talnetant); and D-4418; (xx) elastase inhibitors selected from the group consisting of UT-77 and ZD-0892; (xxi) TNF? converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

A compound of the Formula I may also be used in combination with osteoporosis agents such as roloxifene, droloxifene, lasofoxifene or fosomax and immunosuppressant agents such as FK-506, rapamycin, cyclosporine, azathioprine, and methotrexate.

A compound of the Formula I may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

A compound of the Formula I can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

If formulated as a fixed dose such combination products employ a compound of the Formula I within the dosage range described herein and the other pharmaceutically-active agent within its approved dosage range. Sequential use is contemplated when a combination formulation is inappropriate.

Although a compound of the Formula I is primarily of value as a therapeutic agent for use in warm-blooded animals (including man), it is also useful whenever it is required to inhibit the effects of cytokines. Thus, it is useful as pharmacological standard for use in the development of new biological tests and in the search for new pharmacological agents.

The invention will now be illustrated in the following non-limiting Example in which, unless otherwise stated:—

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) the structure of a compound of the Formula I of the invention was confirmed by nuclear magnetic resonance (NMR) and mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; q, quartet; m, multiplet; br, broad;

(vi) melting points are uncorrected and were determined using a Mettler SP62 automatic melting point apparatus or an oil-bath apparatus; and (vii) the following abbreviations have been used:—

| DMA | N,N-dimethylacetamide |
|---|---|
| DMF | N,N-dimethylformamide |
| DCM | dichloromethane |
| DMSO | dimethylsulphoxide |
| THF | tetrahydrofuran |
| HATU | O-(7-Azabenzotriazol-1-yl)-N,N,N',N'-tetramethyluronium hexafluorophosphate |
| DIPEA | N,N'-diisopropylethylamine |
| HOBT | 1-hydroxybenzotriazole hydrate |
| EDAC | 1-(3-dimethylaminopropyl)-3-ethylcarbodiimide |

EXAMPLE 1

3-{[4-(benzyloxy)benzoyl]amino}-N-cyclopropyl-4-methylbenzamide

To a solution of 4-benzyloxybenzoic acid (11.0 g, 48 mmol) in DCM (100 mL) at 0° C. was added oxalyl chloride (8.4 mL, 96 mmol) followed by DMF (two drops). The resulting mixture was stirred at room temperature for 2 hours. The mixture was evaporated giving a white solid which was dissolved in DCM (50 mL). The resulting solution was added portionwise to a stirred solution of 3-amino-N-cyclopropyl-4-methylbenzamide (7.61 g, 40 mmol) and pyridine (7.76 mL, 96 mmol) in DCM (100 mL) at 0° C. The resulting mixture was stirred at room temperature for 2 hours. The solid was collected by filtration and washed three times with DCM to give the title compound as a white solid (13.9 g, 87%);

NMR Spectrum: (DMSOd$_6$) 0.60 (m, 4H), 2.25 (s, 3H), 2.84 (m, 1H), 5.20 (s, 2H), 7.14 (d, 2H), 7.39 (m, 6H), 7.63 (d, 1H), 7.79 (s, 1H), 7.97 (d, 2H), 8.37 (s, 1H), 9.82 (s, 1H); Mass Spectrum: M+H$^+$ 399.

The 3-amino-N-cyclopropyl-4-methylbenzamide used as starting material was prepared as follows:—

A) To a stirred solution of 4-methyl-3 nitrobenzoyl chloride (20 g) in methylene chloride (200 mL) at 0° C. was added a mixture of cyclopropylamine (7.62 mL) and triethylamine (28 mL). The mixture was allowed to warm to room temperature and stirred for a further 16 hours. The reaction mixture was evaporated in vacuo and a saturated aqueous solution of sodium bicarbonate was added. The precipitated solid was filtered off and washed with isohexane and dried (magnesium sulphate) to give N-cyclopropyl-4-methyl-3-nitrobenzamide as a colourless solid (22.9 g); NMR Spectrum: (DMSOd$_6$) 0.60 (m, 2H), 0.72 (m, 2H), 2.56 (s, 3H), 2.87 (m, 1H), 7.60 (d, 1H), 8.06 (m, 1H), 8.41 (d, 1H), 8.67 (d, 1H); Mass Spectrum: M+H$^+$ 221.

B) A suspension of N-cyclopropyl-4-methyl-3-nitrobenzamide (22.92 g) and 10% palladium on carbon (2 g) in absolute alcohol (500 mL) was agitated under a hydrogen atmosphere for 16 hours. The reaction mixture was filtered through diatomaceous earth (Celite®) and the filtrate evaporated to dryness to give the title compound as a colourless solid (17.1 g); NMR Spectrum: (DMSOd$_6$) 0.53 (m, 2H), 0.65 (m, 2H), 2.07 (s, 3H), 2.80 (m, 1H), 6.92 (m, 2H), 7.06 (d, 1H), 8.09 (d, 1H); Mass Spectrum: M+H$^+$ 191.

EXAMPLE 2

Using an analogous procedure to that described in Example 1, the appropriate starting material was reacted with oxalyl chloride followed by 3-amino-N-cyclopropyl-4-methylbenzamide to give the compounds described in Table 1.

TABLE 1

| R$^3$ | R$^4$ | Method | Note |
|---|---|---|---|
| Benzyloxy | H | Ex 1 | a |
| Methoxy | Benzyloxy | Ex 1 | b |
| Methyl | Benzyloxy | Ex 1 | c |
| Fluoro | Benzyloxy | Ex 1 | d |

Notes
a The product gave the following data; NMR Spectrum: (DMSOd$_6$) 0.57 (m, 2H), 0.69 (m, 2H), 2.29 (s, 3H), 2.86 (m, 1H), 5.22 (s, 2H), 7.25 (m, 1H), 7.42 (m, 7H), 7.62 (m, 2H), 7.83 (s, 1H), 8.41 (s, 1H), 9.99 (s, 1H); Mass Spectrum: M – H$^-$ 399.
b The product gave the following data; NMR Spectrum: (DMSOd$_6$) 0.57 (m, 2H), 0.69 (m, 2H), 2.28 (s, 3H), 2.86 (m, 1H), 3.86 (m, 3H), 5.22 (s, 2H), 7.17 (m, 1H), 7.41 (m, 6H), 7.63 (m, 3H), 7.79 (m, 1H), 8.37 (m, 1H), 9.86 (s, 1H); Mass Spectrum: M – H$^-$ 429. The 4-(benzyloxy)-3-methoxybenzoic acid used as starting material was prepared as follows:-To a stirred solution of 4-hydroxy-3-methoxybenzoic acid (5 g, 30 mmol) in THF (15 mL) was added a solution of sodium hydroxide (3 g) in water (37.5 mL). The resulting mixture was cooled to 0° C. and a solution of benzyl chloride (4.1 mL, 34.8 mmol) in THF (15 mL) was added. The resulting mixture was allowed to warm to room temperature then heated to 70° C. for 18 hours then to 90° C. for 4 hours. The mixture was cooled and evaporated. The residual aqueous mixture was washed with isohexane then acidified with 2M hydrochloric acid solution. The resulting precipitate was collected by filtration, washed with isohexane and dried giving the title compound (5.76 g, 74%); NMR Spectrum: (DMSOd$_6$) 3.83 (s, 3H), 5.19 (s, 2H), 7.14 (m, 1H), 7.40 (m, 6H), 7.55 (dd, 1H), 12.69 (m, 1H); Mass Spectrum: M – H$^-$ 257.
c The product gave the following data; NMR Spectrum: (DMSOd$_6$) 0.57 (m, 2H), 0.68 (m, 2H), 2.26 (m, 6H), 2.85 (m, 1H), 5.27 (s, 2H), 7.15 (m, 1H), 7.34 (m, 2H), 7.42 (m, 2H), 7.50 (m, 2H), 7.63 (m, 1H), 7.78 (m, 1H), 7.85 (m, 2H), 8.40 (m, 1H), 9.84 (s, 1H); Mass Spectrum: M + H$^+$ 415.
d The product gave the following data; NMR Spectrum: (DMSOd$_6$) 0.57 (m, 2H), 0.68 (m, 2H), 2.25 (s, 3H), 2.85 (m, 1H), 5.32 (s, 2H), 7.42 (m, 7H), 7.65 (dd, 1H), 7.83 (m, 3H), 8.41 (d, 1H), 9.97 (s, 1H); Mass Spectrum: M + H$^+$ 419. The 4-(benzyloxy)-3-fluorobenzoic acid used as starting material was prepared from 4-hydroxy-3-fluorobenzoic acid using an analogous procedure to that used to prepare 4-(benzyloxy)-3-methoxybenzoic acid; NMR Spectrum: (DMSOd$_6$) 5.24 (s, 2H), 7.21 (m, 1H), 7.45 (m, 5H), 7.71 (m, 2H); Mass Spectrum: M – H$^-$ 245.

EXAMPLE 3

4-(benzyloxy)-3-chloro-N-{5-[(cyclopropylamino) carbonyl]-2-methylphenyl}benzamide To a solution of 4-(benzyloxy)-3-chlorobenzoic acid (1.5 g, 5.73 mmol) in DMF (11.5 mL) was added 1-(3-dimethylaminopropyl)-3-ethylcarbodiimide hydrochloride (2.2 g, 11.5 mmol), hydroxybenztriazole (1.55 g, 11.5 mmol) and N-methyl-morpholine (2.28 mL) followed by 3-amino-N-cyclopropyl-4-methylbenzamide (1.09 g, 5.73 mmol). The resulting mixture was stirred at room temperature for 48 hours. The mixture was evaporated. A saturated aqueous solution of potassium carbonate was added, the resulting precipitate was collected by filtration, washed with dilute hydrochloric acid then saturated aqueous potassium carbonate solution, then triturated with diethyl ether giving the title compound as a solid (2.0 g, 81%); NMR Spectrum: (DMSOd$_6$) 0.57 (m, 2H), 0.69 (m, 2H), 2.27 (s, 3H), 2.85 (m, 1H), 5.35 (s, 2H), 7.39 (m, 5H), 7.51 (m, 2H), 7.65 (m, 1H), 7.78 (m, 1H), 7.97 (m, 1H), 8.10 (m, 1H), 8.40 (m, 1H), 10.01 (s, 1H); Mass Spectrum: M+H$^+$ 435.

The 4-(benzyloxy)-3-chlorobenzoic acid used as starting material was prepared from 4-hydroxy-3-chlorobenzoic acid using an analogous procedure to that used to prepare 4-(benzyloxy)-3-methoxybenzoic acid (paragraph (b) in the Notes section of Example 2). NMR Spectrum: (DMSOd$_6$) 5.21 (s, 2H), 7.14 (d, 1H), 7.34 (m, 1H), 7.41 (m, 2H), 7.48 (m, 2H), 7.80 (dd, 1H), 7.92 (d, 1H); Mass Spectrum: M–H$^-$ 261.

EXAMPLE 4

N-cyclopropyl-4-methyl-3-{[4-(pyridin-2-ylmethoxy)benzoyl]amino}benzamide

To a stirred solution of N-cyclopropyl-3-[(4-hydroxybenzoyl)amino]-4-methylbenzamide (500 mg, 1.61 mmol) in DMF (2.5 mL) was added potassium carbonate (446 mg, 3.22 mmol). The resulting mixture was stirred at room temperature for 15 minutes. 2-Chloromethyl-pyridine hydrochloride (291 mg, 1.78 mmol) was added and the resulting mixture stirred and heated to 50° C. for 18 h. The mixture was cooled to room temperature and saturated aqueous potassium carbonate solution (15 mL) and ethyl acetate (5 mL) were added. The resulting mixture was stirred for 20 minutes. The solid was collected by filtration, washed with saturated aqueous potassium carbonate solution, ethyl acetate and isohexane and dried giving the title compound as a solid (425 mg, 60%); NMR Spectrum: (DMSOd$_6$) 0.56 (m, 2H), 0.68 (m, 2H), 2.29 (s, 3H), 2.86 (m, 1H), 5.33 (s, 2H), 7.16 (m, 2H), 7.34 (m, 2H), 7.55 (m, 1H), 7.62 (m, 1H), 7.81 (s, 1H), 7.86 (m, 1H), 7.98 (m, 2H), 8.36 (s, 1H), 8.60 (m, 1H), 10.00 (s, 1H); Mass Spectrum: M+H$^+$ 401.

The N-cyclopropyl-3-[(4-hydroxybenzoyl)amino]-4-methylbenzamide used as starting material was prepared as follows:—

To a stirred solution of 3-{[4-(benzyloxy)benzoyl]amino}-N-cyclopropyl-4-methylbenzamide (11.5 g, 28.8 mmol) in methanol (250 mL) was added 10% palladium on carbon (1.1 g) under argon. The argon atmosphere was replaced with hydrogen (balloon) and the resulting mixture stirred at room temperature for 18 h. The mixture was filtered through diatomaceous earth (Celite®) and the filtrate evaporated to dryness to give the title compound as a colourless solid (8.26 g, 92%); NMR Spectrum: (DMSOd$_6$) 0.57 (m, 2H), 0.68 (m, 2H), 2.28 (s, 3H), 2.86 (m, 1H), 6.87 (m, 2H), 7.32 (m, 1H), 7.62 (m, 1H), 7.81 (s, 1H), 7.88 (m, 2H), 8.36 (m, 1H), 9.74 (s, 1H), 10.31 (s, 1H); Mass Spectrum: M–H$^-$ 309.

EXAMPLE 5

Using an analogous procedure to that described in Example 4, the appropriate starting materials were reacted to give the compounds described in Table 2.

TABLE 2

| R$^3$ | R$^4$ | Method | Note |
|---|---|---|---|
| H | 1,3-thiazol-4-ylmethoxy | Ex 4 | a |
| H | pyridin-3-ylmethoxy | Ex 4 | b |
| H | (5-methylisoxazol-3-yl)methoxy | Ex 4 | c |
| H | (5-chloro-1,2,3-thiadiazol-4-yl)methoxy | Ex 4 | d |
| H | imidazo[1,2-a]pyridin-2-ylmethoxy | Ex 4 | e |
| H | (2-methyl-1,3-thiazol-4-yl)methoxy | Ex 4 | f |
| H | (3,5-dimethylisoxazol-4-yl)methoxy | Ex 4 | g |
| H | 1,2,5-thiadiazol-3-ylmethoxy | Ex 4 | h |
| H | (2-carbomethoxy-furan-5-yl)methoxy | Ex 4 | i |
| H | (2-chloro-1,3-thiazol-5-yl)methoxy | Ex 4 | j |
| 1,3-thiazol-4-ylmethoxy | H | Ex 4 | k |
| (2-methyl-1,3-thiazol-4-yl)methoxy | H | Ex 4 | l |
| pyridin-2-ylmethoxy | H | Ex 4 | m |
| (3,5-dimethylisoxazol-4-yl)methoxy | H | Ex 4 | n |
| 1,2,5-thiadiazol-3-ylmethoxy | H | Ex 4 | o |
| (2-chloro-1,3-thiazol-5-yl)methoxy | H | Ex 4 | p |
| Methoxy | pyridin-2-ylmethoxy | Ex 4 | q |
| Methoxy | 1,3-thiazol-4-ylmethoxy | Ex 4 | r |
| Methyl | pyridin-2-ylmethoxy | Ex 4 | s |
| Methyl | 1,3-thiazol-4-ylmethoxy | Ex 4 | t |
| Methyl | (2-methyl-1,3-thiazol-4-yl)methoxy | Ex 4 | u |
| Methyl | (3,5-dimethylisoxazol-4-yl)methoxy | Ex 4 | v |
| Methyl | 1,2,5-thiadiazol-3-ylmethoxy | Ex 4 | w |
| Methyl | (2-carbomethoxy-furan-5-yl)methoxy | Ex 4 | x |
| Fluoro | pyridin-2-ylmethoxy | Ex 4 | y |
| Fluoro | (2-methyl-1,3-thiazol-4-yl)methoxy | Ex 4 | z |
| Fluoro | (3,5-dimethylisoxazol-4-yl)methoxy | Ex 4 | aa |
| Fluoro | 1,2,5-thiadiazol-3-ylmethoxy | Ex 4 | ab |
| Fluoro | 1,3-thiazol-4-ylmethoxy | Ex 4 | ac |
| Fluoro | imidazo[1,2-a]pyridin-2-ylmethoxy | Ex 4 | ad |
| Chloro | pyridin-2-ylmethoxy | Ex 4 | ae |
| Chloro | 1,3-thiazol-4-ylmethoxy | Ex 4 | af |
| H | 5-cyclopropyl-1,3,4-thiadiazol-2-ylmethoxy | Ex 4 | ag |
| H | 6-bromopyridin-2-ylmethoxy | Ex 4 | ah |
| H | 6-methylpyridin-2-ylmethoxy | Ex 4 | ai |
| H | 4-methanesulfonylbenzyloxy | Ex 4 | aj |
| H | 6-methoxycarbonylpyridin-2-ylmethoxy | Ex 4 | ak |

Notes a The product gave the following data; NMR Spectrum: (DMSOd$_6$) 0.58 (m, 2H), 0.68 (m, 2H), 2.30 (s, 3H), 2.85 (m, 1H), 5.37 (s, 2H), 7.18 (m, 2H), 7.33 (m, 1H), 7.64 (m, 1H), 7.83 (m, 2H), 7.99 (m, 2H), 8.39 (m, 1H), 9.17 (s, 1H), 9.90 (s, 1H); Mass Spectrum: M – H$^-$ 406.
b The product gave the following data; NMR Spectrum: (DMSOd$_6$) 0.58 (m, 2H), 0.69 (m, 2H), 2.30 (s, 3H), 2.86 (m, 1H), 5.31 (s, 2H), 7.17 (m, 2H), 7.33 (m, 1H), 7.45 (m, 1H), 7.63 (m, 1H), 7.83 (s, 1H), 7.91 (m, 1H), 8.00 (m, 1H), 8.36 (m, 1H), 8.57 (m, 1H), 8.71 (m, 1H), 9.85 (s, 1H); Mass Spectrum: M + H$^+$ 402.
c The product gave the following data; NMR Spectrum: (DMSOd$_6$) 0.57 (m, 2H), 0.68 (m, 2H), 2.28 (s, 3H), 2.44 (s, 3H), 2.85 (m, 1H), 5.28 (s, 2H), 6.37 (s, 1H), 7.15 (m, 2H), 7.31 (m, 1H), 7.60 (m, 1H), 7.82 (s, 1H), 7.99 (m, 2H), 8.41 (s, 1H), 10.40 (s, 1H); Mass Spectrum: M – H$^-$ 404.
d The product gave the following data; NMR Spectrum: (DMSOd$_6$) 0.58 (m, 2H), 0.68 (m, 2H), 2.29 (s, 3H), 2.86 (m, 1H), 5.62 (s, 2H), 7.24 (m, 2H), 7.34 (m, 1H), 7.64 (m, 1H), 7.83 (s, 1H), 8.01 (m, 2H), 8.37 (m, 1H), 9.95 (s, 1H); Mass Spectrum: M – H$^-$ 441.
e The product gave the following data; NMR Spectrum: (DMSOd$_6$) 0.56 (m, 2H), 0.66 (m, 2H), 2.27 (s, 3H), 2.84 (m, 1H), 5.32 (s, 2H), 6.89 (m, 1H), 7.24 (m, 4H), 7.56 (m, 2H), 7.81 (s, 1H), 7.98 (m, 3H), 8.38 (m, 1H), 8.53 (m, 1H), 9.94 (s, 1H); Mass Spectrum: M + H$^+$ 441.
f The product gave the following data; NMR Spectrum: (DMSOd$_6$) 0.56 (m, 2H), 0.67 (m, 2H), 2.28 (s, 3H), 2.68 (s, 3H), 2.84 (m, 1H), 5.21 (s, 2H), 7.15 (m, 2H), 7.32 (m, 1H), 7.61 (m, 1H), 7.81 (s, 1H), 7.97 (d, 2H), 8.37 (m, 1H), 9.88 (s, 1H); Mass Spectrum: M + H$^+$ 422.
g The product gave the following data; NMR Spectrum: (DMSOd$_6$) 0.58 (m, 2H), 0.69 (m, 2H), 2.25 (s, 3H), 2.26 (s, 3H), 2.45 (s, 3H), 2.85 (m, 1H), 5.04 (s, 2H), 7.15 (d, 2H), 7.34 (d, 1H), 7.64 (m, 1H), 7.82 (s, 1H), 8.00 (d, 2H), 8.37 (m, 1H), 9.85 (s, 1H); Mass Spectrum: M + H$^+$ 420.
h The product gave the following data; NMR Spectrum: (DMSOd$_6$) 0.57 (m, 2H), 0.69 (m, 2H), 2.29 (s, 3H), 2.86 (m, 1H), 5.58 (s, 2H), 7.20 (d, 2H), 7.34 (d, 1H), 7.64 (m, 1H), 7.82 (s, 1H), 8.00 (d, 2H), 8.37 (d, 1H), 9.01 (s, 1H), 9.87 (s, 1H); Mass Spectrum: M – H$^-$ 407.
i The product gave the following data; NMR Spectrum: (DMSOd$_6$) 0.58 (m, 2H), 0.69 (m, 2H), 2.29 (s, 3H), 2.86 (m, 1H), 3.85 (s, 3H), 5.30 (s, 2H), 6.84 (d, 1H), 7.18 (d, 2H), 7.33 (m, 2H), 7.64 (m, 1H), 7.82 (s, 1H), 7.99 (d, 2H), 8.37 (m, 1H), 9.88 (s, 1H); Mass Spectrum: M – H$^-$ 447.
j The product gave the following data; NMR Spectrum: (DMSOd$_6$) 0.57 (m, 2H), 0.69 (m, 2H), 2.28 (s, 3H), 2.86 (m, 1H), 5.47 (s, 2H), 7.17 (d, 2H), 7.34 (d, 1H), 7.64 (m, 1H), 7.80 (m, 1H), 7.85 (m, 1H), 7.99 (m, 2H), 8.37 (m, 1H), 9.87 (s, 1H); Mass Spectrum: M – H$^-$ 440.
k The product gave the following data; NMR Spectrum: (DMSOd$_6$) 0.58 (m, 2H), 0.69 (m, 2H), 2.29 (s, 3H), 2.86 (m, 1H), 5.34 (s, 2H), 7.29 (m, 1H), 7.35 (m, 1H), 7.47 (m, 1H), 7.60 (m, 1H), 7.66 (m, 2H), 7.82 (m, 2H), 8.38 (m, 1H), 9.15 (m, 1H), 9.99 (s, 1H); Mass Spectrum: M + H$^+$ 408. The N-cyclopropyl-3-[(3-hydroxybenzoyl)amino]-4-methylbenzamide used as starting material was prepared from 3-{[3-(benzyloxy)benzoyl]amino}-N-cyclopropyl-4-methylbenzamide using an analogous procedure to that used to prepare N-cyclopropyl-3-[(4-hydroxybenzoyl)amino]-4-methylbenzamide (Method section of Example 4). The product gave the following data; NMR Spectrum: (DMSOd$_6$) 0.57 (m, 2H), 0.69 (m, 2H), 2.26 (s, 3H), 2.86 (m, 1H), 6.99 (m, 1H), 7.37 (dd, 4H), 7.64 (dd, 1H), 7.80 (d, 1H), 8.37 (d, 1H), 9.80 (d, 2H); Mass Spectrum: M – H$^-$ 309.
l The product gave the following data; NMR Spectrum: (DMSOd$_6$) 0.58 (m, 2H), 0.69 (m, 2H), 2.29 (s, 3H), 2.67 (m, 3H), 2.86 (m, 1H), 5.22 (s, 2H), 7.27 (m, 1H), 7.35 (m, 1H), 7.46 (m, 1H), 7.58 (m, 2H), 7.65 (m, 2H), 7.81 (m, 1H), 8.38 (m, 1H), 9.99 (s, 1H); Mass Spectrum: M + H$^+$ 422.
m The product gave the following data; NMR Spectrum: (DMSOd$_6$) 0.57 (m, 2H), 0.69 (m, 2H), 2.29 (s, 3H), 2.86 (m, 1H), 5.30 (s, 2H), 7.27 (m, 1H), 7.36 (m, 2H), 7.47 (m, 1H), 7.61 (m, 4H), 7.81 (m, 1H), 7.86 (m, 1H), 8.38 (m, 1H), 8.60 (m, 1H), 9.98 (m, 1H); Mass Spectrum: M + H$^+$ 402.
n The product gave the following data; NMR Spectrum: (DMSOd$_6$) 0.57 (m, 2H), 0.69 (m, 2H), 2.25 (s, 3H), 2.27 (s, 3H), 2.44 (s, 3H), 2.86 (m, 1H), 5.02 (s, 2H), 6.90 (s, 1H), 7.24 (m, 1H), 7.35 (d, 1H), 7.47 (t, 1H), 7.63 (m, 2H), 7.80 (d, 1H), 8.38 (d, 1H), 9.97 (s, 1H); Mass Spectrum: M + H$^+$ 442.
o The product gave the following data; Mass Spectrum: M – H$^-$ 407.
p The product gave the following data; NMR Spectrum: (DMSOd$_6$) 0.57 (m, 2H), 0.69 (m, 2H), 2.27 (s, 3H), 2.86 (m, 1H), 5.46 (s, 2H), 7.27 (dd, 1H), 7.35 (d, 1H), 7.48 (m, 1H), 7.64 (m, 3H), 7.82 (m, 2H), 8.38 (d, 1H), 9.98 (s, 1H); Mass Spectrum: M + H$^+$ 409.
q The product gave the following data NMR Spectrum: (DMSOd$_6$) 0.57 (m, 2H), 0.68 (m, 2H), 2.27 (s, 3H), 2.86 (m, 1H), 3.90 (s, 3H), 5.29 (s, 2H), 7.17 (d, 1H), 7.36 (m, 2H), 7.59 (m, 4H), 7.79 (m, 1H), 7.87 (m, 1H), 8.42 (m, 1H), 8.60 (m, 1H), 9.98 (s, 1H); Mass Spectrum: M + H$^+$ 432. The N-{5-[(cyclopropylamino)carbonyl]-2-methylphenyl}-4-hydroxy-3-methoxybenzamide used as starting material was prepared from 4-(benzyloxy)-N-{5-[(cyclopropylamino)carbonyl]-2-methylphenyl}-3-methoxybenzamide using an analogous procedure to that used to prepare N-cyclopropyl-3-[(4-hydroxybenzoyl)amino]-4-methylbenzamide (Methods section of Example 4). The product gave the following data; NMR Spectrum: (DMSOd$_6$) 0.57 (m, 2H), 0.69 (m, 2H), 2.28 (s, 3H), 2.86 (m, 1H), 3.85 (s, 3H), 6.88 (d, 1H), 7.33 (d, 1H), 7.52 (dd, 1H), 7.57 (d, 1H), 7.64 (dd, 1H), 7.79 (d, 1H), 8.36 (d, 1H), 9.63 (s, 1H), 9.74 (s, 1H); Mass Spectrum: M + H$^+$ 341.
r The product gave the following data; NMR Spectrum: (DMSOd$_6$) 0.57 (m, 2H), 0.68 (m, 2H), 2.28 (s, 3H), 2.86 (m, 1H), 3.87 (s, 3H), 5.32 (s, 2H), 7.25 (d, 1H), 7.33 (m, 1H), 7.62 (m, 3H), 7.81 (m, 2H), 8.42 (m, 1H), 9.16 (m, 1H), 10.04 (s, 1H); Mass Spectrum: M + H$^+$ 438.

TABLE 2-continued

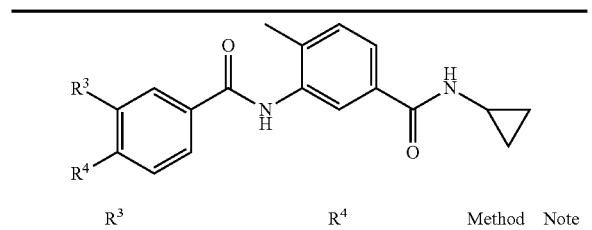

| R³ | R⁴ | Method | Note |
|----|----|----|----| s The product gave the following data; NMR Spectrum: (DMSOd₆) 0.57 (m, 2H), 0.69 (m, 2H), 2.28 (s, 3H), 2.35 (s, 3H), 2.86 (m, 1H), 5.33 (s, 2H), 7.14 (m, 1H), 7.35 (m, 2H), 7.56 (m, 2H), 7.64 (m, 2H), 7.83 (m, 4H), 8.36 (m, 1H), 8.61 (m, 1H), 9.81 (s, 1H); Mass Spectrum: M + H⁺ 416. The N-{5-[(cyclopropylamino)carbonyl]-2-methylphenyl}-4-hydroxy-3-methylbenzamide used as starting material was prepared from 4-(benzyloxy)-N-{5-[(cyclopropylamino)carbonyl]-2-methylphenyl}-3-methylbenzamide using an analogous procedure to that used to prepare N-cyclopropyl-3-[(4-hydroxybenzoyl)amino]-4-methylbenzamide (Methods section of Example 4). The product gave the following data; NMR Spectrum: (DMSOd₆) 0.56 (m, 2H), 0.68 (m, 2H), 2.21 (s, 3H), 2.27 (s, 3H), 2.85 (d, 1H), 6.87 (m, 1H), 7.32 (m, 1H), 7.62 (m, 1H), 7.70 (m, 1H), 7.79 (s, 2H), 8.40 (m, 1H), 9.72 (s, 1H), 10.02 (s, 1H); Mass Spectrum: M + H⁺ 325.
t The product gave the following data; NMR Spectrum: (DMSOd₆) 0.57 (m, 2H), 0.69 (m, 2H), 2.26 (m, 6H), 2.86 (m, 1H), 5.38 (s, 2H), 7.24 (m, 1H), 7.33 (m, 1H), 7.63 (m, 1H), 7.83 (m, 4H), 8.37 (m, 1H), 9.15 (m, 1H), 9.84 (s, 1H); Mass Spectrum: M + H⁺ 422.
u The product gave the following data; NMR Spectrum: (DMSOd₆) 0.57 (m, 2H), 0.68 (m, 2H), 2.24 (m, 6H), 2.68 (m, 3H), 2.86 (m, 1H), 5.25 (s, 2H), 7.22 (m, 1H), 7.33 (m, 1H), 7.59 (s, 1H), 7.64 (m, 1H), 7.79 (m, 1H), 7.85 (m, 2H), 8.40 (m, 1H), 9.85 (s, 1H); Mass Spectrum: M + H⁺ 436.
v The product gave the following data; NMR Spectrum: (DMSOd₆) 0.57 (m, 2H), 0.70 (m, 2H), 2.22 (s, 3H), 2.28 (s, 6H), 2.46 (s, 3H), 2.85 (m, 1H), 5.06 (s, 2H), 7.19 (m, 1H), 7.34 (m, 1H), 7.64 (m, 1H), 7.85 (m, 3H), 8.43 (m, 1H), 9.84 (m, 1H); Mass Spectrum: M + H⁺ 434.
w The product gave the following data; NMR Spectrum: (DMSOd₆) 0.57 (m, 2H), 0.68 (m, 2H), 2.27 (s, 3H), 2.31 (s, 3H), 2.85 (m, 1H), 5.60 (s, 2H), 7.20 (m, 1H), 7.33 (m, 1H), 7.63 (m, 1H), 7.79 (m, 1H), 7.86 (m, 2H), 8.41 (m, 1H), 9.03 (s, 1H), 9.87 (s, 1H); Mass Spectrum: M + H⁺ 423
x The product gave the following data; NMR Spectrum: (DMSOd₆) 0.57 (m, 2H), 0.69 (m, 2H), 2.23 (s, 3H), 2.25 (m, 3H), 2.85 (m, 1H), 3.81 (m, 3H), 5.31 (s, 2H), 6.84 (m, 1H), 7.24 (m, 1H), 7.33 (m, 2H), 7.64 (m, 1H), 7.78 (m, 1H), 7.86 (m, 2H), 8.40 (m, 1H), 9.87 (s, 1H); Mass Spectrum: M + H⁺ 463.
y The product gave the following data; NMR Spectrum: (DMSOd₆) 0.57 (m, 2H), 0.68 (m, 2H), 2.28 (s, 3H), 2.86 (m, 1H), 5.41 (s, 2H), 7.38 (m, 3H), 7.56 (m, 1H), 7.64 (m, 1H), 7.84 (m, 4H), 8.40 (m, 1H), 8.61 (m, 1H), 10.04 (m, 1H); Mass Spectrum: M + H⁺ 420. The N-{5-[(cyclopropylamino)carbonyl]-2-methylphenyl}-3-fluoro-4-hydroxybenzamide used as starting material was prepared from 4-(benzyloxy)-3-fluoro-N-{5-[(cyclopropylamino)carbonyl]-2-methylphenyl}benzamide using an analogous procedure to that used to prepare N-cyclopropyl-3-[(4-hydroxybenzoyl)amino]-4-methylbenzamide (Methods section of Example 4). The product gave the following data; NMR Spectrum: (DMSOd₆) 0.57 (m, 2H), 0.68 (m, 2H), 2.28 (s, 3H), 2.85 (m, 1H), 7.08 (m, 1H), 7.33 (m, 1H), 7.64 (m, 1H), 7.72 (m, 1H), 7.80 (m, 2H), 8.37 (m, 1H), 10.60 (m, 1H); Mass Spectrum: M − H⁻ 327.
z The product gave the following data; NMR Spectrum: (DMSOd₆) 0.57 (m, 2H), 0.68 (m, 2H), 2.28 (s, 3H), 2.67 (m, 4H), 2.85 (m, 1H), 5.31 (s, 2H), 7.35 (m, 1H), 7.48 (m, 1H), 7.65 (m, 2H), 7.80 (s, 1H), 7.86 (m, 2H), 9.99 (s, 1H); Mass Spectrum: M + H⁺ 440.
aa The product gave the following data; NMR Spectrum: (DMSOd₆) 0.57 (m, 2H), 0.69 (m, 2H), 2.28 (s, 6H), 2.46 (s, 3H), 2.86 (m, 1H), 5.15 (s, 2H), 7.34 (d, 1H), 7.44 (t, 1H), 7.64 (m, 1H), 7.80 (m, 1H), 7.87 (m, 2H), 8.37 (m, 1H), 9.95 (m, 1H); Mass Spectrum: M + H⁺ 438.
ab The product gave the following data; NMR Spectrum: (DMSOd₆) 0.57 (m, 2H), 0.69 (m, 2H), 2.28 (s, 3H), 2.85 (m, 1H), 5.68 (s, 2H), 7.35 (m, 1H), 7.47 (m, 1H), 7.65 (m, 1H), 7.81 (s, 1H), 7.87 (m, 1H), 8.37 (m, 1H), 9.01 (s, 1H), 9.97 (s, 1H); Mass Spectrum: M − H⁻ 425.
ac The product gave the following data; NMR Spectrum: (DMSOd₆) 0.57 (m, 2H), 0.69 (m, 2H), 2.28 (s, 3H), 2.86 (m, 1H), 5.44 (s, 2H), 7.34 (m, 1H), 7.50 (m, 1H), 7.65 (m, 1H), 7.79 (m, 1H), 7.86 (m, 3H), 8.37 (m, 1H), 9.16 (m, 1H), 9.94 (m, 1H); Mass Spectrum: M − H⁻ 424.
ad The product gave the following data; NMR Spectrum: (DMSOd₆) 0.57 (m, 2H), 0.69 (m, 2H), 2.26 (s, 3H), 2.86 (m, 1H), 5.40 (s, 2H), 6.91 (td, 1H), 7.27 (ddd, 1H), 7.34 (m, 1H), 7.55 (t, 2H), 7.65 (dd, 1H), 7.79 (d, 1H), 7.85 (m, 2H), 8.08 (s, 1H), 8.37 (d, 1H), 8.55 (m, 1H), 9.91 (s, 1H); Mass Spectrum: M + H⁺ 459
ae The product gave the following data; NMR Spectrum: (DMSOd₆) 0.57 (m, 2H), 0.68 (m, 2H), 2.27 (s, 3H), 2.86 (m, 1H), 5.42 (s, 2H), 7.33 (m, 1H), 7.39 (m, 2H), 7.61 (m, 2H), 7.79 (m, 1H), 7.89 (m, 1H), 7.97 (m, 1H), 8.12 (m, 1H), 8.36 (m, 1H), 8.61 (m, 1H), 9.98 (m, 1H); Mass Spectrum: M + H⁺ 436. The 3-chloro-N-{5-[(cyclopropylamino)carbonyl]-2-methylphenyl}-4-hydroxybenzamide used as starting material was prepared from 4-(benzyloxy)-3-chloro-N-{5-[(cyclopropylamino)carbonyl]-2-methylphenyl}benzamide using an analogous procedure to that used to prepare N-cyclopropyl-3-[(4-hydroxybenzoyl)amino]-4-methylbenzamide (Methods section of Example 4) except that ethyl acetate was used as the solvent in place of methanol. The product gave the following data; NMR Spectrum: (DMSOd₆) 0.57 (m, 2H), 0.69 (m, 2H), 2.28 (s, 3H), 2.86 (m, 1H), 7.08 (m, 1H), 7.33 (m, 1H), 7.64 (m, 1H), 7.80 (m, 2H), 8.03 (m, 1H), 8.36 (m, 1H), 9.87 (s, 1H), 10.79 (m, 1H); Mass Spectrum: M − H⁻ 343.
af The product gave the following data; NMR Spectrum: (DMSOd₆) 0.57 (m, 2H), 0.68 (m, 2H), 2.28 (s, 3H), 2.86 (m, 1H), 5.46 (s, 2H), 7.33 (d, 1H), 7.48 (d, 1H), 7.62 (dd, 1H), 7.79 (d, 1H), 7.86 (d, 1H), 7.98 (dd, 1H), 8.10 (d, 1H), 8.36 (d, 1H), 9.16 (d, 1H), 9.98 (s, 1H); Mass Spectrum: M − H⁻ 424.
ag The product gave the following data; NMR Spectrum: (DMSOd₆) 0.57 (m, 2H), 0.68 (m, 2H), 1.04 (m, 2H), 1.23 (m, 2H), 2.33 (s, 3H), 2.85 (m, 1H), 5.68 (s, 1H), 5.77 (s, 1H), 7.20 (d, 2H), 7.34 (d, 1H), 7.64 (d, 1H), 7.80 (s, 1H), 7.98 (d, 2H), 8.41 (d, 1H), 8.42 (s, 1H), 9.90 (s, 1H); Mass Spectrum: M + H⁺ 449.
ah The product gave the following data; NMR Spectrum: (DMSOd₆) 0.57 (m, 2H), 0.69 (m, 2H), 2.26 (s, 3H), 2.86 (m, 1H), 5.29 (s, 2H), 7.18 (d, 2H), 7.33 (d, 1H), 7.59 (m, 1H), 7.64 (m, 2H), 7.82 (m, 2H), 8.00 (m, 2H), 8.37 (m, 1H), 9.86 (s, 1H); Mass Spectrum: M + H⁺ 482.
ai The product gave the following data; NMR Spectrum: (DMSOd₆) 0.57 (m, 2H), 0.69 (m, 2H), 2.26 (s, 3H), 2.86 (m, 1H), 5.23 (s, 2H), 7.16 (d, 2H), 7.23 (d, 1H), 7.33 (m, 2H), 7.64 (m, 1H), 7.73 (m, 1H), 7.80 (d, 1H), 8.37 (m, 1H), 9.83 (s, 1H); Mass Spectrum: M + H⁺ 416.
aj The product gave the following data; NMR Spectrum: (DMSOd₆) 0.62 (m, 2H), 0.85 (m, 2H) 2.40 (s, 3H), 2.88 (m, 3H), 3.07 (s, 3H), 5.25 (s, 1H), 6.40 (s, 1H), 7.08 (d, 2H), 7.28 (m, 1H), 7.62 (d, 1H), 7.65 (d, 2H), 7.70 (s, 1H), 7.88 (d, 2H), 7.98 (d, 2H), 8.40 (s, 1H); Mass Spectrum: M + Na⁺ 501.
ak The product gave the following data; NMR Spectrum: (DMSOd₆) 0.56 (m, 2H), 0.68 (m, 2H), 2.24 (s, 3H), 2.84 (m, 1H), 5.38 (s, 2H), 7.16 (d, 2H), 7.31 (d, 1H), 7.62 (dd, 1H), 7.69 (d, 1H), 7.98 (d, 2H), 8.35 (m, 2H), 9.10 (s, 1H), 9.82 (s, 1H); Mass Spectrum: M + H⁺ 460. The methyl 2-chloromethylnicotinate used as starting material was prepared according to Chem. Ber. (1987) 120, 649.

EXAMPLE 6

N-cyclopropyl-3-({4-[(4-methoxypyridin-2-yl)methoxy]benzoyl}amino)-4-methylbenzamide To a stirred solution of N-cyclopropyl-3-[(4-hydroxybenzoyl)amino]-4-methylbenzamide (200 mg, 0.64 mmol) and 4-methoxy-2-hydroxymethylpyridine (500 mg, 3.6 mmol) in dry THF (25 mL) under an argon atmosphere was added successively tributylphosphine (500 mg, 2.5 mmol) and diisopropyl azodicarboxylate (500 mg, 2.5 mmol). The mixture was stirred at 20° C. for 16 hours, then the solvent was evaporated at reduced pressure and the residue purified by silica column chromatography, eluting with a gradient of 0 to 10% methanol in ethyl acetate to give the title compound as a white solid (100 mg); NMR Spectrum: (DMSOd₆) 1.55 (m, 2H), 1.65 (m, 2H), 2.25 (s, 3H), 2.85 (m, 1H), 3.85 (s, 3H), 5.20 (s, 2H), 6.95 (dd, 1H), 7.05 (d, 1H), 7.15 (d, 2H), 7.30 (d, 1H), 7.60 (dd, 1H), 7.80 (s, 1H), 7.95 (d, 2H), 8.35 (d, 1H), 8.40 (broad s, 1H), 9.80 (s, 1H); Mass Spectrum: M+H⁺ 432.

The 4-methoxy-2-hydroxymethylpyridine used as starting material was prepared according to J. Med. Chem. (1995) 38, 4910.

EXAMPLE 7

N-{5-[(cyclopropylamino)carbonyl]-2-methylphenyl}-3,5-difluoro-4-(pyridin-2-ylmethoxy)benzamide A mixture of N-{5-[(cyclopropylamino)carbonyl]-2-methylphenyl}-3,4,5-trifluorobenzamide (100 mg, 0.29 mmol), 2-pyridinylmethanol (400 µl) and potassium t-butoxide (32 mg, 0.29 mmol) in NMP (600 µl) was heated in the microwave at 180° C. for 1.5 hrs. The reaction mixture was cooled and partitioned between saturated aqueous sodium bicarbonate and ethyl acetate. The organic phase was washed with dilute aqueous citric acid. Evaporation of the ethyl acetate gave impure product which was purified on silica column chromatography eluting with 0 to 100% ethyl acetate in isohexane. The solvents were evaporated to give a residue which was dissolved in ethyl acetate, then extracted with dilute hydrochloric acid. The aqueous extracts were basified with saturated aqueous sodium bicarbonate solution and then extracted with ethyl acetate to give the title compound as a solid (29 mg, 23%); NMR Spectrum: (DMSOd₆) 0.58 (m, 2H), 0.69 (m, 2H), 2.25 (s, 3H), 2.85 (m, 1H), 5.36 (s, 2H), 7.37 (m, 2H), 7.64 (m, 2H), 7.84 (m, 4H), 8.40 (m, 1H), 8.56 (m, 1H), 10.14 (s, 1H); Mass Spectrum: M−H⁻ 436.

The N-{5-[(cyclopropylamino)carbonyl]-2-methylphenyl}-3,4,5-trifluorobenzamide used as starting material was prepared as follows:—

To a solution of 3-amino-N-cyclopropyl-4-methylbenzamide (1.06 g, 5.58 mmol) in DMF (11 mL) was added trifluorobenzoic acid (0.983 mg, 5.58 mmol), HOBT (1.51 g, 11.2 mmol) and EDAC hydrochloride (2.14 g, 11.2 mmol) and the resulting mixture was stirred for 16 h. Saturated aqueous sodium bicarbonate was added and the title compound filtered off (1.70 g, 88%).

EXAMPLE 8

N-cyclopropyl-4-methyl-3-({4-[(3-methylpyridin-2-yl)methoxy]benzoyl}amino)benzamide To (3-methylpyridine-2-yl)methanol (157 mg, 1.272 mmol) in DCM (5 mL) was added thionyl chloride (200 µl) and the mixture stirred and heated at reflux for 4 h. The mixture was evaporated to dryness. To the residue was added N-cyclopropyl-3-[(4-hydroxybenzoyl)amino]-4-methylbenzamide (197 mg, 0.636 mmol) and potassium carbonate (176 mg, 1.27 mmol) in acetonitrile (5 mL) and the resulting mixture heated at 80° C. for 16 h. The reaction mixture was cooled and partitioned between saturated aqueous sodium bicarbonate and ethyl acetate. The organic phase was concentrated under reduced pressure. Precipitation with DCM in diethyl ether gave the title compound as a solid (270 mg); NMR Spectrum: (DMSOd$_6$) 0.57 (m, 2H), 0.68 (m, 2H), 2.26 (s, 3H), 2.40 (s, 3H), 2.86 (m, 1H), 5.30 (s, 2H), 7.17 (d, 2H), 7.33 (m, 2H), 7.65 (m, 2H), 7.82 (s, 1H), 7.97 (d, 2H), 8.39 (m, 2H), 9.81 (s, 1H); Mass Spectrum: M+H$^+$ 416.

EXAMPLE 9

N-cyclopropyl-4-methyl-3-{[4-(pyrimidin-2-yl-methoxy)benzoyl]amino}benzamide

The title compound was prepared from 2-pyrimidinemethanol and N-cyclopropyl-3-[(4-hydroxybenzoyl)amino]-4-methylbenzamide according to the method used to prepared Example 8, to give the title compound as a solid (149 mg, 58%); NMR Spectrum: (DMSOd$_6$) 0.56 (m, 2H), 0.67 (m, 2H), 2.24 (s, 3H), 2.84 (m, 1H), 5.37 (s, 2H), 7.09 (d, 2H), 7.31 (d, 1H), 7.47 (m, 1H), 7.61 (m, 1H), 7.78 (d, 1H), 7.93 (d, 2H), 8.35 (m, 1H), 8.83 (m, 2H), 9.80 (s, 1H); Mass Spectrum: M+H$^+$ 403.

EXAMPLE 10

N-cyclopropyl-4-methyl-3-{[4-(pyridazin-3-yl-methoxy)benzoyl]amino}benzamide

To a solution of 3-pyridazinylmethanol (140 mg, 1.27 mmol) in DCM (5 mL) was added thionyl chloride (103 μl, 1.42 mmol) and the resulting mixture stirred at room temperature for 4 h. The solvent was evaporated under reduced pressure and then to the residue in DMSO (4 mL) was added N-cyclopropyl-3-[(4-hydroxybenzoyl)amino]-4-methylbenzamide (197 mg, 0.636 mmol), cesium carbonate (621 mg, 1.91 mmol) and tetrabutylammonium iodide (235 mg, 0.636 mmol) and the resulting mixture stirred at 60° C. for 16 h. The reaction mixture was added to a 20 g SCX column and product eluted with methanol. Concentration under reduced pressure gave impure product which was further purified on silica column chromatography eluting with 0-20% methanol/1% ammonium hydroxide SG 0.88 in ethyl acetate. Evaporation and trituration with DCM and diethyl ether and filtration gave the title compound as a solid (15 mg, 5.9%); NMR Spectrum: (DMSOd$_6$) 0.57 (m, 2H), 0.68 (m, 2H), 2.26 (s, 3H), 2.86 (m, 1H), 5.54 (s, 2H), 7.21 (d, 2H), 7.34 (d, 1H), 7.64 (m, 1H), 7.79 (m, 2H), 7.86 (m, 1H), 7.99 (m, 2H), 8.37 (m, 1H), 9.24 (m, 1H), 9.86 (s, 1H); Mass Spectrum: M−H$^−$ 401.

EXAMPLE 11

N-cyclopropyl-3-({3-[(4-methoxypyridin-2-yl)methoxy]benzoyl}amino)-4-methylbenzamide To a stirred solution of N-cyclopropyl-3-[(3-hydroxybenzoyl)amino]-4-methylbenzamide (200 mg, 0.65 mmol) in acetonitrile (50 mL) was added anhydrous potassium carbonate (220 mg, 1.59 mmol) and 4-methoxy-2-chloromethyl-pyridine hydrochloride (150 mg, 0.75 mmol). The mixture was stirred at reflux for 16 hours, then filtered and the solvent evaporated at reduced pressure to give a gum, which was dissolved in ethyl acetate/methanol (19:1, 20 mL) and purified by chromatography on silica, eluting with ethyl acetate/methanol (9:1) to give the compound as a white solid (250 mg, 90%); NMR Spectrum: (CDCl$_3$) 0.60 (m, 2H), 0.80 (m, 2H), 2.32 (s, 3H), 2.86 (m, 1H), 3.85 (s, 3H), 5.19 (s, 2H), 6.67 (s, 1H), 6.75 (dd, 1H), 7.04 (d, 1H), 7.17 (dd, 1H), 7.21 (d, 1H), 7.38 (dd, 1H), 7.48 (d, 1H), 7.54 (m, 2H), 8.02 (s, 1H), 8.14 (s, 1H), 8.40 (d, 1H); Mass spectrum: M+H$^+$ 432.

The 4-methoxy-2-chloromethyl-pyridine hydrochloride used as starting material was prepared according to *J. Med. Chem.* (1995) 38, 4913.

EXAMPLE 12

N-cyclopropyl-3-({4-[(5-hydroxypyridin-2-yl)methoxy]benzoyl}amino)-4-methylbenzamide hydrobromide To a stirred solution of N-cyclopropyl-4-methyl-3-{[4-(5-benzyloxypyridin-2-ylmethoxy)benzoyl]amino}benzamide (1.0 g, 1.97 mmol) in glacial acetic acid (10 mL) was added a solution of HBr (48% in acetic acid, 30 mL). After 6 hours at 25° C. the solution was diluted with ether (100 mL) and the resultant precipitate filtered off and dried to give the title compound as a pale yellow solid (610 mg, 62%); NMR Spectrum: (DMSOd$_6$) 0.56 (m, 2H), 0.68 (m, 2H), 2.25 (s, 3H), 2.84 (m, 1H), 5.36 (s, 2H), 7.18 (d, 2H), 7.31 (d, 1H), 7.63 (dd, 1H), 7.78-7.84 (m, 3H), 8.00 (d, 2H), 8.36 (m, 2H), 9.86 (s, 1H); Mass Spectrum: M+H$^+$ 418.

The N-cyclopropyl-4-methyl-3-{[4-(5-benzyloxypyridin-2-ylmethoxy)benzoyl]amino}benzamide used as starting material was prepared from 5-benzyloxypyrid-2-ylmethanol (prepared according to *J. Med. Chem.* (1977), 20, 1261) and N-cyclopropyl-3-[(4-hydroxybenzoyl)amino]-4-methylbenzamide according to the procedure used to prepare N-cyclopropyl-3-[(4-{[5-(1,3-dioxolan-2-ylmethoxy)pyridin-2-yl]methoxy}benzoyl)amino]-4-methylbenzamide (Example 14).

EXAMPLE 13

N-cyclopropyl-4-methyl-3-({4-[(1-oxidopyridin-2-yl)methoxy]benzoyl}amino)benzamide N-cyclopropyl-4-methyl-3-{[4-(pyridin-2-ylmethoxy)benzoyl]amino}benzamide (200 mg, 0.5 mmol) was dissolved in dichloromethane (50 mL) and stirred while adding 3-chloroperbenzoic acid (85%, 200 mg). The solution was stirred for one hour at 25° C., then washed twice with sodium bicarbonate solution and dried. The solvent was evaporated to give the title compound as a white solid (120 mg); NMR Spectrum: (DMSOd$_6$) 0.56 (m, 2H), 0.68 (m, 2H), 2.24 (s, 3H), 2.84 (m, 1H), 5.35 (s, 2H), 7.18 (d, 2H), 7.31 (d, 1H), 7.42 (m, 2H), 7.60 (m, 2H), 7.78 (m, 1H), 7.99 (d, 2H), 8.36 (m, 2H), 9.84 (s, 1H); Mass Spectrum: M+H$^+$ 418.

EXAMPLE 14

N-cyclopropyl-3-[(4-{[5-(1,3-dioxolan-2-ylmethoxy)pyridin-2-yl]methoxy}benzoyl)amino]-4-methylbenzamide To a stirred solution of N-cyclopropyl-3-[(4-hydroxybenzoyl)amino]-4-methylbenzamide (3.1 g, 10 mmol) in dry THF (200 mL) at 25° C. was added [5-(1,3-dioxolan-2-ylmethoxy)-pyridin-2-yl]methanol (2.4 g, 11 mmol), triphenylphosphine (2.9 g, 11 mmol) and di-tert-butyl azodicarboxylate (2.6 g, 11 mmol). The solution was stirred for 16 hours, then the solvent was evaporated and the residue dissolved in ethyl acetate/methanol (19:1, 50 mL) and purified by chromatography on silica, eluting with a gradient of 5-20% methanol in ethyl acetate, to give the title compound as a white solid (3.8 g, 76%). NMR Spectrum: (DMSOd$_6$) 0.56 (m, 2H), 0.68 (m, 2H), 2.24 (s, 3H), 2.84 (m, 1H), 3.85 (m, 2H), 3.92 (m, 2H), 4.10 (m, 2H), 5.20 (m, 3H), 7.12 (d, 2H), 7.30 (d, 1H), 7.45 (s, 2H), 7.62 (dd, 1H), 7.78 (s, 1H), 7.95 (d, 2H), 8.30 (s, 1H), 8.35 (d, 1H), 9.80 (s, 1H); Mass Spectrum: M+H$^+$ 504.

The [5-(1,3-dioxolan-2-ylmethoxy)-pyridin-2-yl]methanol used as starting material was prepared as follows:—

To a stirred solution of [5-(1,3-dioxolan-2-ylmethoxy)pyridin-2-yl]methyl acetate (6.5 g, 25.7 mmol) in ethanol (100 mL) was added sodium hydroxide (1.2 g, 30 mmol) and the mixture refluxed for 1 hour. The solvent was evaporated at reduced pressure and the residue was partitioned between water (100 mL) and ethyl acetate (100 mL). The organic layer was separated, dried and evaporated to give the title compound as a solid (5.4 g, 99%); NMR Spectrum: (DMSOd$_6$) 3.84 (m, 2H), 3.95 (m, 2H), 4.06 (m, 2H), 4.48 (d, 2H), 5.19 (t, 1H), 5.28 (broad t, 1H), 7.37 (m, 2H), 8.18 (s, 1H); Mass Spectrum: M+H$^+$ 212.

The [5-(1,3-dioxolan-2-ylmethoxy)pyridin-2-yl]methyl acetate used as starting material was prepared as follows:—

A solution of 5-(1,3-dioxolan-2-ylmethoxy)-2-methylpyridine 1-oxide (10 g, 47.4 mmol) in acetic anhydride (100 mL) was stirred at reflux for 2 hours. The reaction was cooled and the solvent evaporated at reduced pressure. The residue was purified by chromatography on silica eluting with 50% hexane/ethyl acetate to give an oil (6.8 g, 57%); NMR Spectrum: (CDCl$_3$) 2.12 (s, 3H), 3.94-4.10 (m, 6H), 5.15 (s, 2H), 5.28 (t, 1H), 7.16 (m, 2H), 8.32 (d, 1H); Mass Spectrum: M+H$^+$ 254.

The 5-(1,3-dioxolan-2-ylmethoxy)-2-methylpyridine 1-oxide used as starting material was prepared as follows:—

To a stirred solution of 5-(1,3-dioxolan-2-ylmethoxy)-2-methylpyridine (20 g, 0.1 mole) in dichloromethane (200 mL) was added portionwise 3-chloroperbenzoic acid (~80% peracid, 24 g, 0.11 mole) during 10 minutes. The mixture was stirred for 1 hour, washed twice with 2N sodium hydroxide (100 mL) and the organic layer was dried over anhydrous magnesium sulphate. Evaporation of the solvent gave the title compound as a white solid (15.4 g, 73%); NMR Spectrum: (DMSOd$_6$) 2.24 (s, 3H), 3.83 (m, 2H), 3.93 (m, 2H), 4.05 (m, 1H), 5.16 (t, 1H), 6.97 (dd, 1H), 7.34 (d, 1H), 8.08 (d, 1H); Mass Spectrum: M+H$^+$ 212.

The 5-(1,3-dioxolan-2-ylmethoxy)-2-methylpyridine used as starting material was prepared as follows:—

To a stirred solution of 2-methyl-5-hydroxypyridine (16.0 g, 0.147 mole) in dry DMF (100 mL) at 25° C. was added portionwise sodium hydride (60% dispersion in oil, 6.0 g, 0.15 mole) during 10 minutes. To the mixture was added 2-bromomethyl-1,3-dioxolane (16.0 mL, 0.154 mole) and the resulting mixture heated at 100° C. for 12 hours, cooled to 25° C. and diluted with ice/water (400 g). The product was extracted into diethyl ether (400 mL), dried over anhydrous magnesium sulphate, and the solvent evaporated at reduced pressure to give the title compound as an oil (25 g, 87%); NMR Spectrum: (CDCl$_3$) 2.50 (s, 3H), 3.94-4.04 (m, 6H), 5.27 (t, 1H), 7.05 (d, 1H), 7.15 (dd, 1H), 8.22 (d, 1H); Mass Spectrum: M+H$^+$ 196.

EXAMPLE 15

N-cyclopropyl-3-{[4-({5-[2-(dimethylamino)ethoxy]pyridin-2-yl}methoxy)benzoyl]amino}-4-methylbenzamide To a stirred solution of N-cyclopropyl-3-[(4-{[5-(1,3-dioxolan-2-ylmethoxy)pyridin-2-yl]methoxy}benzoyl)amino]-4-methylbenzamide (1.0 g, 2 mmol) in methanol (20 mL) was added hydrochloric acid (36% aqueous solution, 10 mL). After 2 hours the solution was basified by addition of 2N sodium hydroxide (55 mL). The precipitate was filtered off and dissolved in THF (100 mL), then stirred while adding a solution of dimethylamine (2M in THF, 2 mL, 4 mmol), titanium isopropoxide (3 mL, 10 mmol) and sodium triacetoxyborohydride (2.2 g, 10 mmol). After 16 hours the mixture was basified with 2N sodium hydroxide, stirred for 10 minutes and the top layer decanted. The lower layer was stirred with THF (50 mL) and decanted again, the combined top layers were dried over magnesium sulphate. The title compound was isolated by chromatography on silica, eluting with a gradient of 0-30% methanol in ethyl acetate to give a gum (120 mg); NMR Spectrum: (CDCl$_3$) 0.60 (m, 2H), 0.83 (m, 2H), 2.32 (s, 3H), 2.40 (s, 6H), 2.82 (t, 2H), 2.90 (m, 1H), 4.17 (t, 2H), 5.20 (s, 2H), 6.60 (s, 1H), 7.06 (d, 2H), 7.26 (dd, 2H), 7.42 (d, 1H), 7.56 (d, 1H), 7.86 (d, 2H), 7.90 (s, 1H), 8.10 (s, 1H), 8.32 (s, 1H); Mass Spectrum: M+H$^+$ 489.

EXAMPLE 16

5-(benzyloxy)-N-{5-[(cyclopropylamino)carbonyl]-2-methylphenyl}pyridine-2-carboxamide The title compound was prepared from 5-(benzyloxy)pyridine-2-carboxylic acid and 3-amino-N-cyclopropyl-4-methylbenzamide according to the method described for Example 1; NMR Spectrum: (DMSOd$_6$) 0.58 (m, 2H), 0.69 (m, 2H), 2.32 (s, 3H), 2.86 (m, 1H), 5.32 (s, 2H), 7.39 (m, 4H), 7.51 (m, 2H), 7.57 (m, 1H), 7.71 (m, 1H), 8.13 (m, 1H), 8.22 (m, 1H), 8.36 (m, 1H), 8.48 (s, 1H), 10.16 (s, 1H); Mass Spectrum: M+Na$^+$ 424.

EXAMPLE 17

N-{5-[(cyclopropylamino)carbonyl]-2-methylphenyl}-5-(pyridin-2-ylmethoxy)pyridine-2-carboxamide The title compound was prepared from N-{5-[(cyclopropylamino)carbonyl]-2-methylphenyl}-5-hydroxypyridine-2-carboxamide and 2-chloromethyl-pyridine hydrochloride according to the method described for Example 4; NMR Spectrum: (DMSOd$_6$) 0.58 (m, 2H), 0.69 (m, 2H), 2.32 (s, 3H), 2.86 (m, 1H), 5.40 (s, 2H), 7.33 (m, 1H), 7.39 (m, 1H), 7.58 (m, 2H), 7.72 (m, 1H), 7.88 (m, 1H), 8.13 (m, 1H), 8.21 (m, 1H), 8.36 (m, 1H), 8.51 (m, 1H), 8.61 (m, 1H), 10.14 (s, 1H); Mass Spectrum: M+H$^+$ 403.

The N-{5-[(cyclopropylamino)carbonyl]-2-methylphenyl}-5-hydroxypyridine-2-carboxamide used as starting material was prepared from 5-(benzyloxy)-N-{5-[(cyclopropylamino)carbonyl]-2-methylphenyl}pyridine-2-carboxamide according to the method used to prepare N-cyclopropyl-3-[(4-hydroxybenzoyl)amino]-4-methylbenzamide from 3-{[4-(benzyloxy)benzoyl]amino}-N-cyclopropyl-4-methylbenzamide (methods section of Example 4).

EXAMPLE 18

N-{5-[(cyclopropylamino)carbonyl]-2-methylphenyl}-5-(pyridin-2-ylmethoxy)pyrazine-2-carboxamide To 2-pyridinylmethanol (300 μL) was added sodium hydride 60% dispersion in oil (20 mg, 1.39 mmol) under inert atmosphere and the mixture stirred at room temperature for 10 minutes. NMP (600 μL) was then added followed by 5-chloro-N-{5-[(cyclopropylamino)carbonyl]-2-methylphenyl}-2-pyrazinecarboxamide (100 mg, 0.303 mmol) and the resulting mixture stirred for 48 hrs. The solvent was evaporated under reduced pressure and the residue partitioned between saturated aqueous sodium bicarbonate and DCM. Evaporation of DCM, precipitation with diethyl ether and isohexanes and filtration gave the title compound as a solid (25 mg, 20%); NMR Spectrum: (DMSOd$_6$) 0.58 (m, 2H), 0.69 (m, 2H), 2.31 (s, 3H), 2.86 (m, 1H), 5.59 (s, 2H), 7.36 (m, 2H), 7.55 (m, 1H), 7.62 (d, 1H), 7.86 (m, 1H), 8.08 (m, 1H), 8.37 (m, 1H), 8.58 (m, 2H), 8.89 (s, 1H), 9.76 (s, 1H); Mass Spectrum: M+H$^+$ 404.

The 5-chloro-N-{5-[(cyclopropylamino)carbonyl]-2-methylphenyl}-2-pyrazinecarboxamide used as starting material was prepared as follows:—

To 5-hydroxypyrazine-2-carboxylic acid (1 g, 1.14 mmol) was added phosphorous oxychloride (10 mL) and phosphorous pentachloride (4.91 g). After the initial reaction had subsided the mixture was heated to 100° C. and stirred for 16 h. The mixture was cooled and formic acid (347 mL, 9.19 mmol) was added to convert all excess phosphorous pentachloride to phosphorous oxychloride then the excess phosphorous oxychloride was carefully evaporated off to give a residue which was dissolved in DCM (50 mL). Triethylamine (10 mL) and 3-amino-N-cyclopropyl-4-methylbenzamide (1.307 g) were added and the resulting mixture stirred at room temperature for 16 h. The solvent was evaporated under reduced pressure and the residue purified on a 20 g silica chromatography column, eluting with 20% methanol/1% ammonium hydroxide SG 0.88 in ethyl acetate. The crude product was dissolved in DCM and washed with saturated aqueous sodium bicarbonate and evaporated to dryness to give the title compound as a solid (1.24 g, 52.6%); NMR Spectrum: (DMSOd6) 0.62 (m, 2H), 0.74 (m, 2H), 2.37 (s, 3H), 2.91 (m, 1H), 7.41 (m, 1H), 7.70 (m, 1H), 8.05 (m, 1H), 8.44 (m, 1H), 9.02 (m, 1H), 9.18 (m, 1H), 10.44 (s, 1H); Mass Spectrum: M−H− 329.

EXAMPLE 19

N-{5-[(cyclopropylamino)carbonyl]-2-methylphenyl}-6-(pyridin-2-ylmethoxy)nicotinamide To 2-pyridinylmethanol (1 mL) was added sodium hydride 60% dispersion in oil (122 mg, 3.05 mmol) under inert atmosphere and the resulting mixture was stirred for 10 minutes then added to a mixture of 6-chloro-N-{5-[(cyclopropylamino)carbonyl]-2-methylphenyl}nicotinamide (334 mg, 1.02 mmol) and copper (I) iodide in collidine (3 mL). The resulting mixture was stirred at room temperature for 30 minutes then at 100° C. for 4 h. The mixture was cooled to room temperature, ethyl acetate was added and the mixture filtered. The filtrates were concentrated under reduced pressure and purified by silica column chromatography eluting with 0 to 100% ethyl acetate in isohexane. Trituration with diethyl ether gave the title compound as a colourless solid (105.6 mg, 26%); NMR Spectrum: (DMSOd$_6$) 0.59 (m, 2H), 0.67-0.71 (m, 2H), 2.27 (s, 3H), 2.86 (m, 1H), 5.53 (s, 2H), 7.10 (d, 1H), 7.35 (m, 2H), 7.48 (m, 1H), 7.65 (m, 1H), 7.82 (m, 2H), 8.29 (m, 1H), 8.37 (m, 1H), 8.58 (m, 1H), 8.80 (d, 1H), 9.99 (s, 1H); Mass Spectrum: M+H$^+$ 403.

The 6-chloro-N-{5-[(cyclopropylamino)carbonyl]-2-methylphenyl}nicotinamide used as starting material was prepared as follows:—

To a solution of 6-chloronicotinyl chloride (7.5 g, 42.61 mmol) in DCM (125 mL) cooled in ice was added a mixture of 3-amino-N-cyclopropyl-4-methylbenzamide (5 g, 26.31 mmol) and triethylamine (11.30 mL, 81.07 mmol) in DCM (125 mL). The resulting mixture was stirred for 16 h at room temperature. The mixture was concentrated under reduced pressure and the residue partitioned between DCM and saturated aqueous potassium carbonate solution. The organic phase was concentrated under reduced pressure and the residue triturated with diethyl ether and isohexane and filtered to give the title compound as a solid (10.56 g); NMR Spectrum: (DMSOd$_6$) 0.57 (m, 2H), 0.69 (m, 2H), 2.28 (s, 3H), 2.85 (m, 1H), 7.36 (m, 1H), 7.70 (m, 2H), 7.83 (s, 1H), 8.38 (m, 2H), 8.98 (s, 1H), 10.24 (s, 1H); Mass Spectrum: M−H− 328.

EXAMPLE 20

N-{5-[(cyclopropylamino)carbonyl]-2-methylphenyl}-2-(pyridin-2-ylmethoxy)pyrimidine-5-carboxamide To a solution of 2-pyridinylmethanol (258 μl, 2.67 mmol) in THF (50 mL) cooled in ice bath to 0° C. was added dropwise lithium hexamethyldisilazide (1M solution in THF, 2.67 mL, 2.67 mmol) and the resulting mixture stirred for 30 minutes at 0° C. N-{5-[(cyclopropylamino)carbonyl]-2-methylphenyl}-2-(methylsulfonyl)pyrimidine-5-carboxamide (1 g, 2.67 mmol) was added and the resulting mixture stirred for 16 h at room temperature. The reaction mixture was concentrated under reduced pressure and the residue partitioned between water and DCM. Concentration of the organic phase under reduced pressure and crystallisation from acetonitrile gave the title compound as a colourless solid (132 mg, 12%); NMR Spectrum: (DMSOd$_6$) 0.57 (m, 2H), 0.69 (m, 2H), 2.30 (s, 3H), 2.86 (m, 1H), 5.61 (s, 2H), 7.36 (m, 2H), 7.49 (m, 1H), 7.66 (m, 1H), 7.85 (m, 2H), 8.38 (m, 1H), 8.58 (m, 1H), 9.16 (s, 2H), 10.16 (s, 1H); Mass Spectrum: M+H$^+$ 404.

The N-{5-[(cyclopropylamino)carbonyl]-2-methylphenyl}-2-(methylsulfonyl)pyrimidine-5-carboxamide used as starting material was prepared as follows:—

To a mixture of N-{5-[(cyclopropylamino)carbonyl]-2-methylphenyl}-2-(methylthio)pyrimidine-5-carboxamide (3.04 g, 8.82 mmol) in methanol (160 mL) cooled in ice bath to 0° C. was added slowly a solution of Oxone® (11.93 g, 19.40 mmol) in water (57 mL) maintaining temperature below 10° C. and the resulting mixture stirred for 16 hrs at room temperature. The methanol was evaporated and the residue partitioned between water and ethyl acetate. The organic phase was washed with brine and concentrated under reduced pressure to give the title compound as a solid (2.385 g, 72%); NMR Spectrum: (DMSOd$_6$) 0.58 (m, 2H), 0.69 (m, 2H), 2.33 (s, 3H), 2.86 (m, 1H), 3.49 (s, 3H), 7.38 (d, 1H), 7.69 (m, 1H), 7.92 (s, 1H), 8.42 (m, 1H), 9.54 (s, 2H), 10.56 (s, 1H); Mass Spectrum: M−H− 373.

The N-{5-[(cyclopropylamino)carbonyl]-2-methylphenyl}-2-(methylthio)pyrimidine-5-carboxamide used as starting material was prepared as follows:—

To a solution of 2-(methylthio)pyrimidine-5-carboxylic acid (1.50 g, 8.82 mmol) and 3-amino-N-cyclopropyl-4-methylbenzamide (1.68 g, 8.82 mmol) in DMF (7.5 mL) was added HATU (3.69 g, 9.70 mmol) and DIPEA (4.30 mL, 26.46 mmol) and the resulting mixture stirred for 16 h at room temperature. Saturated aqueous sodium bicarbonate was added and the mixture extracted with ethyl acetate, washed with brine and concentrated under reduced pressure to give the title compound as a solid (3.04 g, 100%); NMR Spectrum: (DMSOd$_6$) 0.57 (m, 2H), 0.69 (m, 2H), 2.28 (s, 3H), 2.60 (s, 3H), 2.86 (m, 1H), 7.36 (m, 1H), 7.65 (m, 1H), 7.85 (m, 1H), 8.39 (m, 1H), 9.12 (s, 2H), 10.18 (m, 1H); Mass Spectrum: M−H' 341.

The 2-(methylthio)pyrimidine-5-carboxylic acid used as starting material was prepared as follows:—

To a solution of ethyl 2-(methylthio)-5-pyrimidinecarboxylate (2.68 g, 13.53 mmol) in ethanol (18.6 mL) was added potassium hydroxide (1.304 g, 23.28 mmol) and the resulting mixture stirred for 20 minutes at room temperature. The solvent was evaporated under reduced pressure and the residue partitioned between water and diethyl ether. The aqueous phase was then acidified with dilute aqueous hydrochloric acid and the resulting solid filtered off to give the title compound as a solid (1.96 g, 85.2%); NMR Spectrum: (DMSOd$_6$) 2.58 (m, 3H), 9.01 (s, 2H), 13.54 (m, 1H).

The ethyl 2-(methylthio)-5-pyrimidinecarboxylate used as starting material was prepared as follows:—

To a solution of ethyl 4-chloro-2-methylthiopyrimidine-5-carboxylate (5 g, 21.49 mmol) in THF (25 mL) was carefully added zinc powder (4.213 g, 64.46 mmol) and the resulting mixture heated to reflux. Glacial acetic acid (1.23 mL, 21.49 mmol) was added and the reaction mixture stirred and heated for 6 h. The mixture was cooled and filtered through diatomaceous earth (Celite®) and the filtrate evaporated to dryness to give a solid residue which was triturated with DCM and isohexane. The filtrate was evaporated to dryness to give the title compound as a solid (2.68 g, 63%); NMR Spectrum: (DMSOd$_6$) 1.33 (t, 3H), 2.59 (s, 3H), 4.35 (q, 2H), 9.03 (s, 2H).

EXAMPLE 21

N-{5-[(cyclopropylamino)carbonyl]-2-methylphenyl}-2-(imidazo[1,2-a]pyridin-2-ylmethoxy)pyrimidine-5-carboxamide A mixture of N-{5-[(cyclopropylamino)carbonyl]-2-methylphenyl}-2-(methylsulfonyl)pyrimidine-5-carboxamide (120 mg, 0.32 mmol), imidazo[1,2-a]pyridine-2-methanol (48 mg, 0.32 mmol) and potassium carbonate (44 mg, 0.32 mmol) in THF (5 mL) was heated to 67° C. for 3.5 h. The mixture was cooled to room temperature and partitioned between DCM and water and the layers separated. The aqueous layer was extracted with DCM and the combined organic extracts dried (MgSO$_4$), filtered and concentrated at reduced pressure to give a yellow oil. This material was purified by silica column chromatography, eluting with a gradient of 0 to 8% methanol in DCM to give the title compound as a white solid (33 mg, 23%); NMR Spectrum: (DMSOd$_6$) 0.57 (m, 2H), 0.67 (m, 2H), 2.27 (s, 3H), 2.83 (m, 1H), 5.70 (s, 2H), 7.26 (t, 1H), 7.35 (d, 1H), 7.66 (m, 2H), 7.78 (d, 1H), 7.83 (d, 1H), 8.30 (s, 1H), 8.38 (d, 1H), 8.75 (d, 1H), 9.17 (s, 2H), 10.16 (s, 1H); Mass Spectrum: m-H⁻ 441, 443.

The imidazo[1,2-a]pyridine-2-methanol used as starting material was prepared as follows:—

To a mixture of imidazo[1,2-a]pyridine-2-carboxylic acid ethyl ester (500 mg, 2.63 mmol) in THF (10 mL) at 5° C. was added 1M LiAlH$_4$ in THF (2.63 mL, 2.63 mmol) dropwise under argon. The mixture was stirred at 5° C. for 1 h and then quenched by the addition of ethyl acetate (5 mL) and stirred for a further 15 min. The mixture was partitioned between DCM and water and the layers separated. The organic layer was washed with brine, dried (MgSO$_4$), filtered and concentrated at reduced pressure to give a yellow oil. This material was purified by silica column chromatography, eluting with a gradient of 0 to 10% methanol in DCM to give the title compound as a colourless oil (130 mg, 33%); NMR Spectrum: (CDCl$_3$); 3.30 (br s, 1H), 4.85 (s, 2H), 6.77 (t, 1H), 7.16 (1H, dt), 7.54 (1H, s), 7.57 (1H, s), 8.08 (d, 1H).

EXAMPLE 22

N-{5-[(cyclopropylamino)carbonyl]-2-methylphenyl}-2-(1,3-thiazol-4-ylmethoxy)pyrimidine-5-carboxamide To a solution of thiazole-4-methanol (79 mg) in THF (1 mL) at 0° C. under argon was added 1M lithium bis(trimethylsilyl)amide in THF (0.35 mL). After 30 minutes N-{5-[(cyclopropylamino)carbonyl]-2-methylphenyl}-2-(methylsulfonyl)pyrimidine-5-carboxamide (127 mg, 0.34 mmol) in THF (3 mL) was added and the reaction warmed to room temperature and stirred for 5 hours. The reaction mixture was partitioned between ethyl acetate and water, the organic phases washed with brine, dried (Na$_2$SO$_4$) and concentrated. The residue was purified by flash chromatography on a 12 g silica cartridge eluting with a gradient of 0 to 5% Methanol/DCM to give the title compound as a solid (31 mg, 23%); NMR Spectrum: (DMSOd$_6$) 0.56 (m, 2H), 0.69 (m, 2H), 2.29 (s, 3H), 2.85 (m, 1H), 5.63 (s, 2H), 7.36, (d, 1H) 7.67 (dd, 1H), 7.83 (dd, 2H), 8.49 (d, 1H), 9.14 (m, 2H), 10.14 (s, 1H); Mass Spectrum: M+H⁺ 410.

The thiazole-4-methanol used as a starting material was prepared as follows:—

Lithium aluminium hydride (1M solution THF, 1.5 mL) was added slowly to a stirred solution of ethyl thiazole-4-carboxylate (224 mg) in THF (4 mL) cooled to 0° C. The reaction mixture was stirred and allowed to warm to room temperature over 1 hour. Ethyl acetate (20 mL) was added to the reaction mixture followed by water (1 mL), 2M NaOH solution (2 mL) then water (3 mL). A precipitate formed which was filtered off through Celite®. The filtrate was concentrated to give the title compound (150 mg, 92%); NMR Spectrum: (DMSOd$_6$) 4.12 (s, 2H), 7.47 (s, 1H), 9.03 (s, 1H).

EXAMPLE 23

Using an analogous procedure to that described in Example 22, the appropriate starting material was reacted with N-{5-[(cyclopropylamino)carbonyl]-2-methylphenyl}-2-(methylsulfonyl)pyrimidine-5-carboxamide to give the compounds described in Table 3.

TABLE 3

| R⁴ | Method | Note |
|---|---|---|
| thiazol-2-ylmethoxy | Ex 22 | a |
| pyrimidin-2-ylmethoxy | Ex 22 | b |
| (1-methyl-1H-imidazol-2-yl)methoxy | Ex 22 | c |

TABLE 3-continued

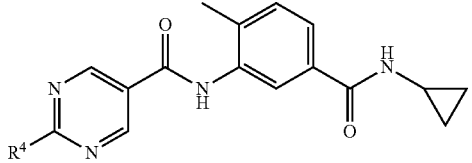

| R⁴ | Method | Note |
| --- | --- | --- |
| (1,5-dimethyl-1H-pyrazol-3-yl)methoxy | Ex 22 | d |
| (1,3-dimethyl-1H-pyrazol-5-yl)methoxy | Ex 22 | e |
| (3-methylpyridin-2-yl)methoxy | Ex 22 | f |
| (1-methyl-1H-benzimidazol-2-yl)methoxy | Ex 22 | g |
| isoquinolin-1-ylmethoxy | Ex 22 | h |
| quinolin-2-ylmethoxy | Ex 22 | i |
| 1,3-benzothiazol-2-ylmethoxy | Ex 22 | j |
| 1-(2-pyridinyl)ethoxy | Ex 22 | k |

Notes
a The product gave the following data: Mass Spectrum: M + H⁺ 410.
b The product gave the following data: NMR Spectrum: (DMSOd₆) 0.50 (m, 2H), 0.61 (m, 2H), 2.23 (s, 3H), 2.50 (s, 3H), 2.78 (m, 1H), 3.27 (s, 1H), 5.65 (s, 2H), 7.27 (d, 1H), 7.37 (t, 1H), 7.57 (d, 1H), 7.78 (s, 1H), 8.28 (d, 1H), 8.71 (d, 2H), 9.05 (s, 1H), 10.07 (s, 1H); Mass Spectrum: M + H⁺ 405.
c The product gave the following data: Mass Spectrum: M + H⁺ 407.
d The product gave the following data: Mass Spectrum: M + H⁺ 421.
e The product gave the following data: Mass Spectrum: M + H⁺ 421.
f The product gave the following data: Mass Spectrum: M + H⁺ 418.
g The product gave the following data: Mass Spectrum: M + H⁺ 457.
h The product gave the following data: Mass Spectrum: M + H⁺ 454.
i The product gave the following data: NMR Spectrum: (DMSOd₆) 0.53 (m, 2H), 0.69 (m, 2H), 2.28 (s, 3H), 2.85 (m, 1H), 5.75 (s, 2H), 7.34, (d, 1H) 7.64 (m, 2H), 7.80 (m, 1H), 7.64 (s, 1H), 8.01 (d, 2H), 8.38 (s, 1H), 8.43 (d, 1H), 9.15 (s, 2H), 10.12 (s, 1H); Mass Spectrum: M + H⁺ 421.
j The product gave the following data: NMR Spectrum: (DMSOd₆) 0.57 (m, 2H), 0.69 (m, 2H), 2.28 (s, 3H), 2.85 (m, 1H), 5.95 (s, 2H), 7.34, (d, 1H) 7.49 (m, 1H), 7.55 (m, 1H), 7.66 (m, 1H), 7.85 (s, 1H), 8.03 (d, 1H), 8.14 (d, 1H), 8.38 (s, 1H), 9.18 (s, 1H), 10.18 (s, 1H); Mass Spectrum: M − H⁻ 458.
k The product gave the following data: Mass Spectrum: M + H⁺ 418.

EXAMPLE 24

N-cyclopropyl-4-methyl-3-{[4-(1-pyridin-2-ylethoxy)benzoyl]amino}benzamide

To 3-{[4-(hydroxy)benzoyl]amino}-N-cyclopropyl-4-methylbenzamide (150 mg, 0.484 mmol) in DCM (20 mL) was added polymer supported triphenyl phosphine (937 mg, 1.45 mmol) and the 1-pyridin-2-ylethanol (45 mg, 0.363 mmol). Diethyl azodicarboxylate (126 mg, 0.726 mmol) was then added dropwise. The reaction was stirred for 17 h at room temperature and was then filtered and the filtrates were evaporated. The crude residue was purified by flash silica chromatography using ethyl acetate in iso-hexane (5-100%) as the eluent to give the title compound as a colourless oil (22 mg, 11%); NMR Spectrum: (DMSOd₆) 0.55 (m, 2H), 0.68 (m, 2H), 1.64 (d, 3H), 2.22 (s, 3H), 2.83 (m, 1H), 5.60 (q, 1H), 7.02 (d, 2H), 7.31 (d, 2H), 7.43 (d, 1H), 7.62 (d, 1H), 7.80 (m, 2H), 7.90 (d, 2H), 8.35 (d, 1H), 8.58 (d, 1H), 9.75 (s, 1H); Mass Spectrum: M+H⁺ 416.

The 1-pyridin-2-ylethanol used as starting material was prepared as follows:—To 1-pyridin-2-ylethanone (600 mg, 3.18 mmol) in methanol (10 mL) was added polymer supported sodium borohydride (3.0 g, 9.92 mmol) and the reaction was stirred at room temperature for 72 h. The reaction was filtered and the filtrates were evaporated to give the 1-pyridin-2-ylethanol as colourless oil (630 mg, quantitative); NMR Spectrum: (DMSOd₆) 1.38 (d, 3H), 4.71 (q, 1H), 5.30 (br, 1H), 7.21 (m, 1H), 7.50 (d, 1H), 7.75 (m, 1H), 8.47 (1H, d); Mass Spectrum: M+H⁺ 192.

EXAMPLE 25

N-cyclopropyl-3-[(4-{[5-(hydroxymethyl)pyridin-2-yl]methoxy}benzoyl)amino]-4-methylbenzamide To a solution of methyl 6-({4-[({5-[(cyclopropylamino)carbonyl]-2-methylphenyl}amino)carbonyl]phenoxy}methyl)nicotinate (200 mg, 0.436) in THF (10 mL) was added LiAlH₄ (33 mg, 0.871 mmol). Extra THF (7 mL) was added and the mixture was stirred for 16 h at room temperature. Glauber's salt (Na₂SO₄.10H₂O) (1.0 g, 3.11 mmol) was added and the reaction was stirred for a further 16 h. The mixture was filtered and the solid washed with methanol (40 mL). The filtrates were evaporated and the resulting crude material was purified by SCX cartridge to give the title compound as a white solid (150 mg, 80%); NMR Spectrum: (DMSOd₆) 0.57 (m, 2H), 0.67 (m, 2H), 2.25 (s, 3H), 2.85 (m, 1H), 4.56 (d, 2H), 5.28 (s, 2H), 5.59 (t, 1H), 7.15 (d, 2H), 7.34 (d, 1H), 7.51 (d, 1H), 7.64 (m, 1H), 7.79 (m, 2H), 7.97 (m, 2H), 8.37 (d, 1H), 8.55 (s, 1H), 9.83 (s, 1H); Mass Spectrum: M+H⁺ 432.

EXAMPLE 26

N-cyclopropyl-3-[(4-{[5-(1-hydroxy-1-methylethyl)pyridin-2-yl]methoxy}benzoyl)amino]-4-methylbenzamide To methyl 6-({4-[({5-[(cyclopropylamino)carbonyl]-2-methylphenyl}amino)carbonyl]phenoxy}methyl)nicotinate (300 mg, 0.654) in THF (10 mL) at 0° C. was added a 3M solution of methyl magnesium bromide in diethyl ether (0.54 mL, 1.62 mmol) dropwise and the resulting mixture stirred while allowing to warm to ambient temperature. After 3 h the reaction was at room temperature and a 3M solution of methyl magnesium bromide in diethyl ether (0.54 mL, 1.62 mmol) was added dropwise. The reaction was stirred at room temperature for 2 h and then a saturated aqueous solution of ammonium chloride (15 mL) was carefully added. The mixture was extracted with DCM (3×20 mL) and the organic layers were combined, filtered and the filtrates evaporated. The resulting crude product was purified by silica flash chromatography using ethyl acetate as the eluent to give a mixture of the product and the corresponding methyl ketone. This was dissolved in DCM (5 mL) and polymer supported tosyl hydrazine (400 mg, 1.07 mmol) and acetic acid (1 drop) were added. After stirring for 16 h at room temperature the reaction had MP carbonate (275 mg, 0.751 mmol) added and was stirred for 30 minutes at room temperature. The mixture was filtered and the solid washed with methanol. The filtrates and washings were combined and evaporated to give the title compound as a white solid (65 mg, 22%); NMR Spectrum: (DMSOd₆) 0.62 (m, 2H), 0.74 (m, 2H), 1.52 (s, 6H), 2.31 (s, 3H), 2.90 (m, 1H), 5.61 (s, 2H), 7.21 (d, 2H), 7.38 (d, 1H), 7.52 (d, 1H), 7.19 (d, 1H), 7.86 (s, 1H), 7.94 (m, 1H), 8.02 (d, 2H), 8.41 (d, 1H), 8.76 (d, 1H), 9.88 (s, 1H); Mass Spectrum: M+H⁺ 460.

EXAMPLE 27

N-cyclopropyl-3-{[4-({5-[(dimethylamino)methyl]pyridin-2-yl}methoxy)benzoyl]amino}-4-methylbenzamide To N-cyclopropyl-3-[(4-{[5-(hydroxymethyl)pyridin-2-yl]methoxy}benzoyl)amino]-4-methylbenzamide (100 mg, 0.232 mmol) in DCM (10 mL) was added Dess-Martin periodinane (197 mg, 0.464 mmol) and the reaction was stirred at room temperature for 3 h. The reaction was diluted with DCM (40 mL), washed with 2N NaOH (3×15 mL) and then a saturated brine solution (20 mL). The DCM solution of the aldehyde was dried with magnesium sulphate and then concentrated under reduced pressure to approximately 10 mL. To this solution was added dimethylamine (2M in THF, 0.13 mL, 0.260 mmol), acetic acid (2 drops) and titanium iso-propoxide (132 mg, 0.464 mmol). The mixture was stirred at room temperature for 1 h and then sodium triacetoxyborohydride (123 mg, 0.580 mmol) was added. The reaction was stirred for 18 h at room temperature. Water (4 drops) was added and the reaction was evaporated to dryness. The residue was purified by basic preparative HPLC to give the title compound as a white solid (30 mg, 28%); NMR Spectrum: (DMSOd$_6$) 0.62 (m, 2H), 0.75 (m, 2H), 2.21 (s, 6H), 2.31 (s, 3H), 2.90 (m, 1H), 3.48 (s, 2H), 5.83 (s, 2H), 7.22 (d, 2H), 7.38 (d, 1H), 7.57 (d, 1H), 7.68 (dd, 1H), 7.81 (m, 1H), 7.85 (d, 1H), 8.04 (d, 2H), 8.42 (d, 1H), 8.57 (s, 1H), 9.88 (s, 1H); Mass Spectrum: M+H$^+$ 459.

EXAMPLE 28

N-cyclopropyl-3-{[4-({5-[(isopropylamino)methyl] pyridin-2-yl}methoxy)benzoyl]amino}-4-methylbenzamide Using an analogous procedure to that described in Example 27, N-cyclopropyl-3-[(4-{[5-(hydroxymethyl)pyridin-2-yl]methoxy}benzoyl)amino]-4-methylbenzamide was oxidised and the resulting aldehyde reacted with isopropylamine to give the title compound; NMR Spectrum: (DMSOd$_6$) 0.58 (m, 2H), 0.68 (m, 2H), 1.00 (d, 6H), 2.25 (s, 3H), 2.70 (m, 1H), 2.86 (m, 1H), 3.71 (s, 2H), 5.76 (s, 2H), 7.14 (d, 2H), 7.33 (d, 1H), 7.49 (d, 1H), 7.64 (m, 1H), 7.80 (m, 2H), 7.99 (d, 2H), 8.40 (d, 1H), 8.55 (s, 1H), 9.87 (s, 1H); Mass Spectrum: M+H$^+$ 473.

EXAMPLE 29

N-cyclopropyl-3-[(4-{[6-(hydroxymethyl)pyridin-2-yl]methoxy}benzoyl)amino]-4-methylbenzamide 3-{[4-(hydroxy)benzoyl]amino}-N-cyclopropyl-4-methylbenzamide (100 mg, 0.323 mmol), [6-(bromomethyl)pyridin-2-yl]methanol (71 mg, 0.355 mmol) and potassium carbonate (49 mg, 0.355 mmol) were mixed in acetonitrile (3 mL) and the reaction was stirred at room temperature for 16 h. The reaction was then heated at 100° C. in the microwave for 10 mins. Water (10 mL) was added and the mixture was extracted with DCM (3×15 mL). The organic layers were combined and evaporated to give a white solid which was triturated with DCM to give the title compound as a white solid (80 mg, 58%); NMR Spectrum: (DMSOd$_6$) 0.58 (m, 2H), 0.68 (m, 2H), 2.25 (s, 3H), 2.85 (m, 1H), 4.59 (s, 2H), 5.24 (s, 2H), 7.16 (d, 2H), 7.32 (d, 1H), 7.38 (d, 1H), 7.45 (d, 1H), 7.63 (m, 1H), 7.80 (m, 2H), 7.97 (d, 2H), 8.36 (d, 1H), 9.82 (s, 1H); Mass Spectrum: M+H$^+$ 432.

EXAMPLE 30

Methyl 6-({4-[({5-[(cyclopropylamino)carbonyl]-2-methylphenyl}amino)carbonyl]phenoxy}methyl) pyridine-2-carboxylate 3-{[4-(hydroxy)benzoyl]amino}-N-cyclopropyl-4-methylbenzamide (200 mg, 0.626 mmol), pyridine (164 mg, 0.710 mmol) and potassium carbonate (98 mg, 0.710 mmol) were mixed in acetonitrile (6 mL) and the reaction was stirred at room temperature for 16 h. The reaction was then heated at 100° C. in the microwave for 20 mins. Water (10 mL) was added and the mixture was extracted with DCM (3×20 mL). The organic layers were combined and evaporated to give a white solid which was triturated with DCM to give the title compound as a white solid (220 mg, 74%); NMR Spectrum: (DMSOd$_6$) 0.58 (m, 2H), 0.68 (m, 2H), 2.26 (s, 3H), 2.85 (m, 1H), 3.92 (s, 3H), 5.37 (s, 2H), 7.19 (d, 2H), 7.32 (d, 1H), 7.63 (m, 1H), 7.80 (m, 2H), 8.05 (m, 4H), 8.38 (d, 1H), 9.85 (s, 1H); Mass Spectrum: M+H$^+$ 460.

EXAMPLE 31

N-cyclopropyl-3-[(4-{[6-(1-hydroxy-1-methylethyl) pyridin-2-yl]methoxy}benzoyl)amino]-4-methylbenzamide To methyl 6-({4-[({5-[(cyclopropylamino)carbonyl]-2-methylphenyl}amino)carbonyl]phenoxy}methyl)pyridine-2-carboxylate (139 mg, 0.303-mmol) in THF (5 mL) at 0° C. was added a 3M solution of methyl magnesium bromide in diethyl ether (0.44 mL, 1.32 mmol) dropwise. The mixture was stirred in the melting ice bath. After 3 h the reaction was at room temperature and a 3M solution of methyl magnesium bromide in diethyl ether (0.50 mL, 1.50 mmol) was added dropwise. The reaction was stirred at room temperature for 72 h and then a saturated aqueous solution of ammonium chloride (15 mL) was carefully added. The mixture was extracted with DCM (3×20 mL) and the organic layers were combined, filtered and the filtrates were evaporated. This crude solid was dissolved in DCM (5 mL) and polymer supported tosyl hydrazine (100 mg, 0.268 mmol) and acetic acid (2 drops) were added and the mixture was stirred for 1 h. The reaction was filtered and the solid washed with methanol (10 mL) and the filtrates and washings were combined and evaporated to dryness. The resulting crude product was purified by silica flash chromatography using ethyl acetate in iso-hexane (50 to 100%) as the eluent to give the title compound as a white solid (47 mg, 34%); NMR Spectrum: (DMSOd$_6$) 0.57 (m, 2H), 0.68 (m, 2H), 1.46 (s, 6H), 2.25 (s, 3H), 2.85 (m, 1H), 5.27 (s, 2H), 7.17 (d, 2H), 7.32 (d, 1H), 7.38 (d, 1H), 7.62 (m, 2H), 7.81 (m, 2H), 7.97 (d, 2H), 8.35 (d, 1H), 9.81 (s, 1H); Mass Spectrum: M+H$^+$ 460.

EXAMPLE 32

N-cyclopropyl-3-({4-[(6-{[2-(diethylamino)ethoxy] methyl}pyridin-2-yl)methoxy]benzoyl}amino)-4-methylbenzamide To a 60% dispersion of NaH in mineral oil (25 mg, 0.625 mmol) in DMA (4 mL) was added N,N-diethylethanolamine (24 mg, 0.205 mmol). The reaction was stirred at room temperature for 20 minutes. A solution of 3-[(4-{[6-(bromomethyl)pyridin-2-yl]methoxy}benzoyl)amino]-N-cyclopropyl-4-methylbenzamide (77 mg, 0.155 mmol) in DMA (2 mL) was added dropwise to the reaction which was then stirred for 1 h at room temperature. The reaction was quenched by the addition of water (1 mL) and was purified by preparative HPLC to give the title compound as a white solid (29 mg, 35%); NMR Spectrum: (DMSOd$_6$) 0.58 (m, 2H), 0.69 (m, 2H), 0.96 (t, 6H), 2.26 (s, 3H), 2.50 (m, 4H), 2.64 (t, 2H), 2.86 (m, 1H), 3.59 (t, 2H), 4.59 (s, 2H), 5.75 (s, 2H), 7.18

(d, 2H), 7.33 (d, 1H), 7.42 (m, 2H), 7.64 (dd, 1H), 7.80 (s, 1H), 7.87 (t, 1H), 7.96 (d, 2H), 8.36 (d, 1H), 9.83 (s, 1H); Mass Spectrum: M+H$^+$ 531.

The 3-[(4-{[6-(bromomethyl)pyridin-2-yl]methoxy}benzoyl)amino]-N-cyclopropyl-4-methylbenzamide used as starting material was prepared as follows:—

To 3-{[4-(hydroxy)benzoyl]amino}-N-cyclopropyl-4-methylbenzamide (1.50 g, 4.84 mmol) and potassium carbonate (3.34 g, 24.2 mmol) in refluxing acetonitrile (20 mL) was added a solution of 2,6-bis(bromomethyl)pyridine (5.13 g, 19.4 mmol) in acetonitrile (10 mL) over 25 mins. The reaction was cooled to room temperature and water (20 mL) was added. The mixture was extracted with DCM (3×30 mL) and the organic layers were combine and evaporated to leave a solid which was triturated with hot ethyl acetate to give 3-[(4-{[6-(bromomethyl)pyridin-2-yl]methoxy}benzoyl)amino]-N-cyclopropyl-4-methylbenzamide as a white solid (1.449 g, 61%); NMR Spectrum: (DMSOd$_6$) 0.58 (m, 2H), 0.70 (m, 2H), 2.27 (s, 3H), 2.85 (m, 1H), 4.73 (s, 2H), 5.30 (s, 2H), 7.19 (d, 2H), 7.32 (d, 1H), 7.49 (d, 1H), 7.55 (d, 1H), 7.65 (d, 1H), 7.81 (s, 1H), 7.90 (t, 1H) 7.98 (d, 2H), 8.38 (d, 1H), 9.85 (s, 1H); Mass Spectrum: M+H$^+$ 494, 496 Br pattern.

EXAMPLE 33

N-cyclopropyl-3-({4-[(6-{[2-(dimethylamino)ethoxy]methyl}pyridin-2-yl)methoxy]benzoyl}amino)-4-methylbenzamide Using an analogous procedure to that described in Example 32, 2-dimethylaminoethanol was reacted with 3-[(4-{[6-(bromomethyl)pyridin-2-yl]methoxy}benzoyl)amino]-N-cyclopropyl-4-methylbenzamide to give the title compound; NMR Spectrum: (DMSOd$_6$) 0.58 (m, 2H), 0.69 (m, 2H), 2.19 (s, 6H), 2.26 (s, 3H), 2.50 (m, 2H), 2.86 (m, 1H), 3.62 (t, 2H), 4.60 (s, 2H), 5.28 (s, 2H), 7.18 (d, 2H), 7.34 (d, 1H), 7.41 (d, 1H), 7.46 (d, 1H), 7.63 (d, 1H), 7.80 (s, 1H), 7.89 (t, 1H), 7.98 (d, 2H), 8.37 (d, 1H), 9.83 (s, 1H); Mass Spectrum: M+H$^+$ 503.

EXAMPLE 34

N-cyclopropyl-3-{[4-({6-[(2-methoxyethyl)amino]pyridin-2-yl}methoxy)benzoyl]amino}-4-methylbenzamide A mixture of N-cyclopropyl-4-methyl-3-({4-[(6-bromo-2-pyridinyl)methoxy]benzoyl}amino)benzamide (100 mg, 0.21 mmol), 2-methoxyethylamine (500 µL) and NMP (500 µL) was heated to 190° C. in the microwave for 90 min. The cooled reaction mixture was eluted through a silica cartridge with isohexane then ethyl acetate to give the crude product which was triturated with diethyl ether to give the title compound as a solid (36 mg); NMR Spectrum: (DMSOd$_6$) 0.57 (m, 2H), 0.68 (m, 2H), 2.27 (s, 3H), 2.85 (m, 1H), 3.28 (m, 2H), 3.31 (m, 3H), 5.08 (s, 2H), 6.47 (d, 1H), 6.61 (d, 2H), 7.14 (d, 2H), 7.32 (m, 2H), 7.40 (m, 1H), 7.63 (m, 1H), 7.80 (m, 2H), 7.97 (m, 2H), 8.37 (m, 1H), 9.84 (s, 1H); Mass Spectrum: M+H$^+$ 475.

EXAMPLE 35

N-cyclopropyl-3-({4-[(6-{[2-(dimethylamino)ethyl]amino}pyridin-2-yl)methoxy]benzoyl}amino)-4-methylbenzamide Using an analogous procedure to that described in Example 34, 2-dimethylaminoethylamine was reacted with N-cyclopropyl-4-methyl-3-({4-[(6-bromo-2-pyridinyl)methoxy]benzoyl}amino)benzamide to give the title compound; NMR Spectrum: (DMSOd$_6$) 0.57 (m, 2H), 0.69 (m, 2H), 2.16 (s, 2H), 2.22 (s, 6H), 2.27 (s, 3H), 2.43 (t, 2H), 2.86 (m, 1H), 5.07 (s, 2H), 6.38 (t, 1H), 6.44 (d, 1H), 6.60 (d, 1H), 7.13 (d, 2H), 7.63 (m, 1H), 7.82 (s, 1H), 7.97 (d, 2H), 8.36 (m, 1H), 9.83 (s, 1H); Mass Spectrum: M+H$^+$ 488.

EXAMPLE 36

N-cyclopropyl-4-methyl-3-({4-[(5-methylisoxazol-3-yl)methoxy]benzoyl}amino)benzamide hydrochloride To a solution of N-cyclopropyl-4-methyl-3-({4-[(5-methylisoxazol-3-yl)methoxy]benzoyl}amino)benzamide (20 mg, 0.05 mmol) in 1:1 DCM and methanol (2.0 mL) was added hydrochloric acid (0.05 mmol). The solvent was evaporated to give the title compound; NMR Spectrum: (DMSOd$_6$) 0.57 (m, 2H), 0.68 (m, 2H), 2.26 (s, 3H), 2.44 (s, 3H), 2.85 (m, 1H), 5.25 (s, 2H), 6.37 (s, 1H), 7.15 (m, 2H), 7.31 (m, 1H), 7.61 (m, 1H), 7.78 (s, 1H), 7.98 (m, 2H), 8.37 (s, 1H), 9.82 (s, 1H); Mass Spectrum: M–H$^-$ 404, M+Na$^+$ 428.

EXAMPLE 37

N-cyclopropyl-4-methyl-3-({4-[(5-methylisoxazol-3-yl)methoxy]benzoyl}amino)benzamide hydrobromide Using an analogous procedure to that described in Example 36, N-cyclopropyl-4-methyl-3-({4-[(5-methylisoxazol-3-yl)methoxy]benzoyl}amino)benzamide was reacted with hydrobromic acid to give the title compound; NMR Spectrum: (DMSOd$_6$) 0.57 (m, 2H), 0.68 (m, 2H), 2.26 (s, 3H), 2.44 (s, 3H), 2.85 (m, 1H), 5.25 (s, 2H), 6.37 (s, 1H), 7.15 (m, 2H), 7.31 (m, 1H), 7.61 (m, 1H), 7.78 (s, 1H), 7.98 (m, 2H), 8.37 (s, 1H), 9.82 (s, 1H); Mass Spectrum: M–$^-$ 404, M+Na$^+$ 428.

EXAMPLE 38

N-cyclopropyl-4-methyl-3-({4-[(5-methylisoxazol-3-yl)methoxy]benzoyl}amino)benzamide methanesulfonate Using an analogous procedure to that described in Example 36, N-cyclopropyl-4-methyl-3-({4-[(5-methylisoxazol-3-yl)methoxy]benzoyl}amino)benzamide was reacted with methanesulfonic acid to give the title compound: NMR Spectrum: (DMSOd$_6$) 0.57 (m, 2H), 0.68 (m, 2H), 2.26 (s, 3H), 2.44 (s, 3H), 2.52 (s, 3H), 2.85 (m, 1H), 5.25 (s, 2H), 6.37 (s, 1H), 7.15 (m, 2H), 7.31 (m, 1H), 7.61 (m, 1H), 7.78 (s, 1H), 7.98 (m, 2H), 8.37 (s, 1H), 9.82 (s, 1H), 12.12 (br s, 1H); Mass Spectrum: M–H$^-$ 404, M+Na$^+$ 428.

EXAMPLE 39

N-cyclopropyl-4-methyl-3-{[4-(pyridin-2-ylmethoxy)benzoyl]amino}benzamide hydrochloride Using an analogous procedure to that described in Example 36, N-cyclopropyl-4-methyl-3-{[4-(pyridin-2-ylmethoxy)benzoyl]amino}benzamide was reacted with hydrochloric acid to give the title compound; NMR Spectrum: (DMSOd$_6$) 0.56 (m, 2H), 0.68 (m, 2H), 2.24 (s, 3H), 2.86 (m, 1H), 5.44 (s, 2H), 7.18 (d, 2H), 7.32 (m, 1H), 7.65

(m, 2H), 7.81 (m, 2H), 7.98 (d, 2H), 8.19 (m, 1H), 8.36 (m, 1H), 8.73 (m, 1H), 9.85 (s, 1H); Mass Spectrum: M+H⁺ 401.

EXAMPLE 40

N-cyclopropyl-4-methyl-3-{[4-(pyridin-2-yl-methoxy)benzoyl]amino}benzamide sulfate Using an analogous procedure to that described in Example 36, N-cyclopropyl-4-methyl-3-{[4-(pyridin-2-yl-methoxy)benzoyl]amino}benzamide was reacted with sulfonic acid to give the title compound; NMR Spectrum: (DMSOd$_6$) 0.56 (m, 2H), 0.68 (m, 2H), 2.24 (s, 3H), 2.86 (m, 1H), 5.46 (s, 2H), 7.18 (d, 2H), 7.32 (m, 1H), 7.62 (m, 1H), 7.75 (m, 2H), 7.89 (m, 1H), 7.99 (d, 2H), 8.36 (m, 2H), 8.80 (m, 1H), 9.85 (s, 1H); Mass Spectrum: M+H⁺ 401.

EXAMPLE 41

N-{5-[(cyclopropylamino)carbonyl]-2-methylphenyl}-3-fluoro-4-(pyridin-2-ylmethoxy)benzamide hydrochloride Using an analogous procedure to that described in Example 36, N-{5-[(cyclopropylamino)carbonyl]-2-methylphenyl}-3-fluoro-4-(pyridin-2-ylmethoxy)benzamide was reacted with hydrochloric acid to give the title compound; NMR Spectrum: (DMSOd$_6$) 0.57 (m, 2H), 0.68 (m, 2H), 2.28 (s, 3H), 2.86 (m, 1H), 5.60 (s, 2H), 7.32 (m, 1H), 7.43 (m, 1H), 7.66 (m, 1H), 7.84 (m, 5H), 8.40 (m, 2H), 8.83 (m, 1H), 10.07 (br s, 1H); Mass Spectrum: M+H⁺ 420.

EXAMPLE 42

N-{5-[(cyclopropylamino)carbonyl]-2-methylphenyl}-3-fluoro-4-(pyridin-2-ylmethoxy)benzamide hydrobromide Using an analogous procedure to that described in Example 36, N-{5-[(cyclopropylamino)carbonyl]-2-methylphenyl}-3-fluoro-4-(pyridin-2-ylmethoxy)benzamide was reacted with hydrobromic acid to give the title compound; NMR Spectrum: (DMSOd$_6$) 0.57 (m, 2H), 0.68 (m, 2H), 2.25 (s, 3H), 2.86 (m, 1H), 5.48 (s, 2H), 7.32 (m, 1H), 7.42 (m, 1H), 7.64 (m, 2H), 7.82 (m, 4H), 8.17 (m, 1H), 8.37 (m, 1H), 8.75 (m, 1H), 9.92 (s, 1H); Mass Spectrum: M+H⁺ 420.

EXAMPLE 43

N-{5-[(cyclopropylamino)carbonyl]-2-methylphenyl}-3-fluoro-4-(pyridin-2-ylmethoxy)benzamide methanesulfonate Using an analogous procedure to that described in Example 36, N-{5-[(cyclopropylamino)carbonyl]-2-methylphenyl}-3-fluoro-4-(pyridin-2-ylmethoxy)benzamide was reacted with methanesulfonic acid to give the title compound; NMR Spectrum: (DMSOd$_6$) 0.57 (m, 2H), 0.68 (m, 2H), 2.25 (s, 3H), 2.40 (s, 3H), 2.86 (m, 1H), 5.51 (s, 2H), 7.32 (m, 1H), 7.42 (m, 1H), 7.63 (m, 1H), 7.73 (m, 1H), 7.78 (s, 1H), 7.86 (m, 3H), 8.25 (m, 1H), 8.37 (m, 1H), 8.78 (m, 1H), 9.95 (s, 1H); Mass Spectrum: M+H⁺ 420.

EXAMPLE 44

2-(1,3-benzothiazol-2-ylmethoxy)-N-{5-[(cyclopropylamino)carbonyl]-2-methylphenyl}pyrimidine-5-carboxamide hydrobromide Using an analogous procedure to that described in Example 36, 2-(1,3-benzothiazol-2-ylmethoxy)-N-{5-[(cyclopropylamino)carbonyl]-2-methylphenyl}pyrimidine-5-carboxamide was reacted with hydrobromic acid to give the title compound; NMR Spectrum: (DMSOd$_6$) 0.57 (m, 2H), 0.69 (m, 2H), 2.28 (s, 3H), 2.85 (m, 1H), 5.10 (s, 2H), 7.34, (d, 1H) 7.49 (m, 1H), 7.55 (m, 1H), 7.66 (m, 1H), 7.76 (s, 1H), 7.99 (d, 1H), 8.10 (d, 1H), 8.38 (s, 1H), 9.11 (s, 2H), 9.19, (s, 1H), 10.09 (s, 1H); Mass Spectrum: M–H⁻ 458.

EXAMPLE 45

2-(1,3-benzothiazol-2-ylmethoxy)-N-{5-[(cyclopropylamino)carbonyl]-2-methylphenyl}pyrimidine-5-carboxamide methanesulfonate Using an analogous procedure to that described in Example 36, 2-(1,3-benzothiazol-2-ylmethoxy)-N-{5-[(cyclopropylamino)carbonyl]-2-methylphenyl}pyrimidine-5-carboxamide was reacted with methanesulfonic acid to give the title compound; NMR Spectrum: (DMSOd$_6$) 0.57 (m, 2H), 0.69 (m, 2H), 2.28 (s, 3H), 2.52 (s, 3H), 2.85 (m, 1H), 5.91 (s, 2H), 7.34, (d, 1H) 7.49 (m, 1H), 7.55 (m, 1H), 7.66 (m, 1H), 7.76 (s, 1H), 7.99 (d, 1H), 8.10 (d, 1H), 8.38 (s, 1H), 9.11 (s, 2H), 9.17, (s, 1H), 10.17 (s, 1H), 10.78 (br s, 1H); Mass Spectrum: M–H⁻ 458.

EXAMPLE 46

N-{5-[(cyclopropylamino)carbonyl]-2-methylphenyl}-5-(pyridin-2-ylmethoxy)pyridine-2-carboxamide hydrobromide Using an analogous procedure to that described in Example 36, N-{5-[(cyclopropylamino)carbonyl]-2-methylphenyl}-5-(pyridin-2-ylmethoxy)pyridine-2-carboxamide was reacted with hydrobromic acid to give the title compound; NMR Spectrum: (DMSOd$_6$) 0.58 (m, 2H), 0.69 (m, 2H), 2.32 (s, 3H), 2.86 (m, 1H), 5.49 (s, 2H), 7.33 (m, 1H), 7.58 (m, 1H), 7.76 (m, 2H), 7.95 (m, 1H), 8.15 (m, 2H), 8.34 (m, 2H), 8.53 (m, 1H), 8.82 (m, 1H), 10.13 (s, 1H); Mass Spectrum: M+H⁺ 403.

The invention claimed is:
1. A compound of the Formula. I

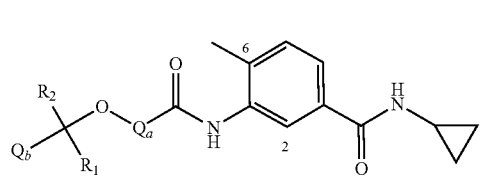

wherein
Q$_a$ is phenyl or heteroaryl, and Q$_a$ may optionally bear 1 or 2 substituents selected from hydroxy, halogeno, trifluoromethyl, cyano, amino, (1-6C)alkyl, (2-6C)alkenyl, (2-6C)alkynyl, (1-6C)alkoxy, (1-6C)alkylamino, di-[(1-6C)alkyl]amino and (1-6C)alkoxycarbonyl;

R₁ and R₂ are each independently selected from hydrogen, (1-6C)alkyl, (2-6C)alkenyl and (2-6C)alkynyl; and $Q_b$ is phenyl, heteroaryl or heterocyclyl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkcyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;

and wherein any of the substituents on $Q_a$ or $Q_b$ defined hereinbefore which comprise a CH₂ group which is attached to 2 carbon atoms or a CH₃ group which is attached to a carbon atom may optionally bear on each said CH₂ or CH₃ group one or more substituents selected from hydroxy, cyano, amino, (1-6C)alkyl, (1-6C)alkoxy, (1-6C)alkylamino and di-[(1-6C)alkyl]amino;

or a pharmaceutically-acceptable salt thereof.

2. A compound of the Formula I according to claim 1 wherein $Q_a$ is phenyl, pyridyl, pyrimidinyl, pyrazinyl or pyridazinyl, and $Q_a$ may optionally bear 1 or 2 substituents selected from halogeno, (1-6C)alkyl and (1-6C)alkoxy;

R₁ and R₂ are each independently selected from hydrogen, (1-6C)alkyl, (2-6C)alkenyl and (2-6C)alkynyl; and $Q_b$ is phenyl, heteroaryl or heterocyclyl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;

and wherein any of the substituents on $Q_a$ or $Q_b$ defined hereinbefore which comprise a CH₂ group which is attached to 2 carbon atoms or a CH₃ group which is attached to a carbon atom may optionally bear on each said CH₂ or CH₃ group one or more substituents selected from hydroxy, cyano, amino, (1-6C)alkyl, (1-6C)alkoxy, (1-6C)alkylamino and di-[(1-6C)alkyl]amino;

or a pharmaceutically-acceptable salt thereof.

3. A compound of the Formula I according to claim 1 or claim 2 wherein $Q_a$ is phenyl, pyridyl, pyrimidinyl, pyrazinyl or pyridazinyl, and $Q_a$ may optionally bear 1 or 2 substituents selected from hydroxy, halogeno, (1-6C)alkyl and (1-6C)alkoxy; or a pharmaceutically-acceptable salt thereof.

4. A compound of the Formula I according to claim 1 or claim 2 wherein $Q_b$ is phenyl or heteroaryl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;

and wherein any of the substituents on $Q_b$ which comprise a CH₂ group which is attached to 2 carbon atoms or a CH₃ group which is attached to a carbon atom may optionally bear on each said CH₂ or CH₃ group one or more substituents selected from hydroxy, cyano, amino, (1-6C)alkyl, (1-6C)alkoxy, (1-6C)alkylamino and di-[(1-6C)alkyl]amino;

or a pharmaceutically-acceptable salt thereof.

5. A compound of the Formula I according to claim 1 or claim 2 wherein $Q_b$ is phenyl, pyridyl, pyrazinyl, pyridazinyl, thiazolyl, thiadiazolyl, imidazolyl, isoxazolyl, oxazolyl, furanyl, thienyl, benzimidazolyl, isoquinolinyl, quinolinyl, benzothiazolyl or pyrido[1,2-a]imidazolyl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(1-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;

and wherein any of the substituents on $Q_b$ which comprise a CH₂ group which is attached to 2 carbon atoms or a CH₃ group which is attached to a carbon atom may optionally bear on each said CH₂ or CH₃ group one or more substituents selected from hydroxy, cyano, amino, (1-6C)alkyl, (1-6C)alkoxy, (1-6C)alkylamino and di-[(1-6C)alkyl]amino;

or a pharmaceutically-acceptable salt thereof.

6. A compound of the Formula I according to claim 1 or claim 2 wherein R₁ and R₂ are each independently selected from hydrogen, (1-6C)alkyl, (2-6C)alkenyl and (2-6C)alkynyl;

or a pharmaceutically-acceptable salt thereof.

7. A compound of the Formula I according to claim 1 or claim 2 wherein R₁ and R₂ are each independently selected from hydrogen and (1-6C)alkyl;

or a pharmaceutically-acceptable salt thereof.

8. A compound of the Formula I according to claim 1 wherein $Q_a$ is phenyl, pyridyl, pyrimidinyl, pyrazinyl or pyridazinyl, and $Q_a$ may optionally bear 1 or 2 substituents selected from halogeno, (1-6C)alkyl and (1-6C)alkoxy;

R₁ and R₂ are each independently selected from hydrogen and (1-6C)alkyl; and $Q_b$ is phenyl, pyridyl, pyrimidinyl, pyrazinyl, pyridazinyl, thiazolyl, thiadiazolyl, imidazolyl, isoxazolyl, oxazolyl, furanyl, thienyl, benzimidazolyl, isoquinolinyl, quinolinyl, benzothiazolyl or pyrido[1,2-a]imidazolyl, and $Q_b$ may optionally bear 1 or 2 substituents selected from hydroxy, halogeno, (1-6C)alkyl, (2-6C)alkenyl, (2-6C)alkynyl, (3-6C)cycloalkyl, (3-6C)cycloalkyl-(1-6C)

alkyl, (1-6C)alkoxy, (3-6C)cycloalkoxy, (3-6C)cycloalkyl-(1-6C)alkoxy, carboxy, (1-6C)alkoxycarbonyl, N-(1-6C)alkylcarbamoyl, N,N-di-[(1-6C)alkyl]carbamoyl, (2-6C)alkanoyl, amino, (1-6C)alkylamino, di-[(-6C)alkyl]amino, halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio, (1-6C)alkylsulphinyl, (1-6C)alkylsulphonyl, aminosulphonyl, N-(1-6C)alkylsulphamoyl, N,N-di-[(1-6C)alkyl]sulphamoyl and (3-6C)cycloalkylsulphonyl;

and wherein any of the substituents on $Q_b$ which comprise a $CH_2$ group which is attached to 2 carbon atoms or a $CH_3$ group which is attached to a carbon atom may optionally bear on each said $CH_2$ or $CH_3$ group one or more substituents selected from hydroxy, cyano, amino, (1-6C)alkyl, (1-6C)alkoxy, (1-6C)alkylamino and di-[(1-6C)alkyl]amino;

or a pharmaceutically-acceptable salt thereof.

9. A process for preparing a compound of the Formula I, or pharmaceutically-acceptable salt thereof which comprises:
(a) reacting a benzoic acid of the Formula II, or a activated derivative thereof,

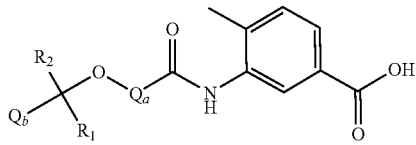

II with an amine of the Formula III

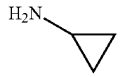

III under standard amide bond forming conditions, wherein $Q_a$, $Q_b$, $R_1$ and $R_2$ are as defined in claim 1 or claim 2 and wherein any functional group is optionally protected, and:
(i) removing any protecting groups; and
(ii) optionally forming a pharmaceutically-acceptable salt; or
(b) reacting an acid of the Formula IV, or an activated derivative thereof,

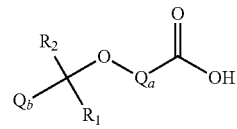

IV with an aniline of the Formula VI

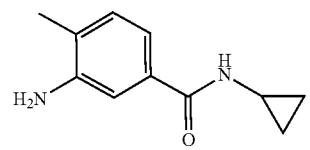

VI under standard amide bond forming, wherein $Q_a$, $Q_b$, $R_1$ and $R_2$ are as defined in claim 1 or claim 2 and wherein any functional group is optionally protected, and:
(i) removing any protecting groups;
(ii) optionally forming a pharmaceutically-acceptable salt; or
(c) for the preparation of a compound of the Formula I wherein a substituent on $Q_a$ or $Q_b$
is (1-6C)alkoxy or substituted (1-6C)alkoxy, (1-6C)alkylamino, di-[(1-6C)alkyl]amino or substituted (1-6C)alkylamino, the alkylation of an amide derivative of the Formula I wherein a substituent on $Q_a$ or $Q_b$ is hydroxy or amino.

* * * * *